(12) United States Patent
Asculai et al.

(10) Patent No.: US 11,382,958 B2
(45) Date of Patent: Jul. 12, 2022

(54) DEBRIDING COMPOSITION FOR TREATING WOUNDS

(71) Applicant: MEDIWOUND LTD., Yavne (IL)

(72) Inventors: Eilon Asculai, Lehavim (IL); Dafna Geblinger, Rehovot (IL); Mery Kleyman, Tel Aviv (IL); Deborah Hanah Bartfeld, Mazkeret-Batya (IL)

(73) Assignee: MediWound Ltd., Yavne (IL)

( * ) Notice: Subject to any disclaimer, the term of this patent is extended or adjusted under 35 U.S.C. 154(b) by 51 days.

(21) Appl. No.: 16/072,955

(22) PCT Filed: Jan. 30, 2017

(86) PCT No.: PCT/IL2017/050107
§ 371 (c)(1),
(2) Date: Jul. 26, 2018

(87) PCT Pub. No.: WO2017/130204
PCT Pub. Date: Aug. 3, 2017

(65) Prior Publication Data
US 2019/0030140 A1    Jan. 31, 2019

Related U.S. Application Data

(60) Provisional application No. 62/289,246, filed on Jan. 31, 2016.

(51) Int. Cl.
*A61K 38/48* (2006.01)
*A61K 47/32* (2006.01)
(Continued)

(52) U.S. Cl.
CPC ........ *A61K 38/4873* (2013.01); *A61K 9/0014* (2013.01); *A61K 9/06* (2013.01);
(Continued)

(58) Field of Classification Search
CPC .... C12Y 304/22032; C12Y 304/22031; C12N 9/64; C12N 9/63; A61L 26/0052;
(Continued)

(56) References Cited

U.S. PATENT DOCUMENTS 4,197,291 A    4/1980   Klein et al.
4,226,854 A    10/1980  Klein et al.
(Continued)

FOREIGN PATENT DOCUMENTS

CN    103285383 A    9/2013
CN    105213107 A    1/2016
(Continued)

OTHER PUBLICATIONS

M. Bishop. Acid Dissociation Constants. Internet Article (2014). (Year: 2014).*
(Continued)

*Primary Examiner* — Sean C. Barron
(74) *Attorney, Agent, or Firm* — Allan A. Fanucci

(57) ABSTRACT

The present invention relates to debriding compositions in the form of an aqueous gel. Particularly, the present invention relates to a debriding composition comprising a proteolytic enzyme mixture obtained from bromelain present in a dry form, and an aqueous gel carrier, wherein, prior to use, the proteolytic enzyme mixture being admixed with the aqueous gel carrier to form a debriding composition useful for debridement and treatment of c wounds.

16 Claims, 6 Drawing Sheets

Before treatment

After 11 treatments

(51) Int. Cl.
| | |
|---|---|
| *A61K 9/00* | (2006.01) |
| *A61K 47/10* | (2017.01) |
| *A61K 9/06* | (2006.01) |
| *A61K 38/54* | (2006.01) |
| *C12N 9/64* | (2006.01) |
| *A61L 26/00* | (2006.01) |
| *A61P 17/02* | (2006.01) |
| *A61K 47/02* | (2006.01) |
| *C12N 9/50* | (2006.01) |

(52) U.S. Cl.
CPC .............. *A61K 38/54* (2013.01); *A61K 47/02* (2013.01); *A61K 47/10* (2013.01); *A61K 47/32* (2013.01); *A61L 26/0014* (2013.01); *A61L 26/0052* (2013.01); *A61L 26/0066* (2013.01); *A61P 17/02* (2018.01); *C12N 9/64* (2013.01); *C12Y 304/22031* (2013.01); *C12Y 304/22032* (2013.01); *A61L 2300/254* (2013.01); *C12N 9/63* (2013.01)

(58) Field of Classification Search
CPC .............. A61L 26/0066; A61L 26/0014; A61L 2300/254; A61P 17/02; A61K 9/0014; A61K 38/54; A61K 47/10; A61K 47/32; A61K 38/4873; A61K 9/06; A61K 47/02; C08L 33/08; C08L 71/02
See application file for complete search history.

(56) References Cited

U.S. PATENT DOCUMENTS

| | | |
|---|---|---|
| 4,286,064 A | 8/1981 | Galbraith |
| 4,307,081 A | 12/1981 | Klein et al. |
| 4,329,430 A | 5/1982 | Klein et al. |
| 4,668,228 A | 5/1987 | Bolton et al. |
| 4,784,653 A | 11/1988 | Bolton et al. |
| 5,271,943 A | 12/1993 | Bogart et al. |
| 5,387,517 A | 2/1995 | Cini |
| 5,514,370 A | 5/1996 | Stern et al. |
| 5,575,987 A | 11/1996 | Kamei et al. |
| 5,804,213 A | 9/1998 | Rolf |
| 5,824,305 A | 10/1998 | Mynott |
| 5,830,739 A | 11/1998 | Houck et al. |
| 5,928,640 A | 7/1999 | Mynott |
| 6,294,365 B1 | 9/2001 | De Rosier et al. |
| 6,335,427 B1 | 1/2002 | Mynott et al. |
| 6,548,556 B2 | 4/2003 | Hobson et al. |
| 6,803,038 B1 | 10/2004 | Maurer et al. |
| 7,794,709 B2 | 9/2010 | Rosenberg |
| 8,062,661 B2 | 11/2011 | Caldwell et al. |
| 8,840,870 B2 | 9/2014 | Tamareselvy et al. |
| 2002/0102253 A1 | 8/2002 | Mynott et al. |
| 2002/0188107 A1 | 12/2002 | Mynott et al. |
| 2009/0010910 A1 | 1/2009 | Toren et al. |
| 2009/0275105 A1 | 11/2009 | Ortiz |
| 2010/0272659 A1 | 10/2010 | Muller et al. |
| 2011/0098267 A1* | 4/2011 | Babu ................... A61K 31/497 514/210.2 |
| 2011/0280853 A1* | 11/2011 | Fallon ................ C11D 3/38636 424/94.2 |
| 2012/0121580 A1 | 5/2012 | Bhambhani et al. |
| 2012/0171187 A1 | 7/2012 | Gorecki et al. |
| 2014/0154229 A1* | 6/2014 | Rosenberg .............. A61P 19/02 424/94.2 |
| 2016/0101165 A1 | 4/2016 | Salamone et al. |

FOREIGN PATENT DOCUMENTS

| | | |
|---|---|---|
| EP | 0 313 346 A2 | 4/1989 |
| JP | 2010538622 A | 12/2010 |
| JP | 2012514604 A | 6/2012 |
| KR | 20030055442 A | 7/2003 |
| RU | 2180856 C1 | 3/2002 |
| RU | 2241489 C2 | 12/2004 |
| RU | 2348396 C2 | 3/2009 |
| WO | 81/01242 A1 | 5/1981 |
| WO | 93/10811 A1 | 6/1993 |
| WO | 00/14253 A1 | 3/2000 |
| WO | 03/090598 A2 | 11/2003 |
| WO | 2006/054309 A2 | 5/2006 |
| WO | 2008/021543 A2 | 2/2008 |
| WO | 2010/038231 A1 | 4/2010 |
| WO | 2013/011514 A1 | 1/2013 |
| WO | 2014150857 A1 | 9/2014 |
| WO | 2017/183018 A1 | 10/2017 |

OTHER PUBLICATIONS

PubChem CID: 24203: Disodium hydrogen phosphate. Created Jun. 24, 2005. (Year: 2005).*
Bala et al. Bromelain Production: Current Trends and Perspective. Archives Des Sciences (2012), 65(11), 369-399. (Year: 2012).*
Secor Jr. et al. LC-MS/MS Identification of a Bromelain Peptide Biomarker from Ananas comosus Merr. Evidence-Based Complementary and Alternative Medicine (2012), Article ID 548486, 10 pages. (Year: 2012).*
Bharadwaj et al., (2011) "Higher Molecular Weight Polyethylene Glycol Increases Cell Proliferation While Improving Barrier Function in an In Vitro Colon Cancer Model;" J Biomed Biotechnol 2011: 587470; 7 pages.
Bhasha et al., (2013) "Recent Trends in Usage of Polymers in the Formulation of Dermatological Gels;" Indian Journal of Research in Pharmacy and Biotechnology 1(2): 161-168.
Eldad et al., (1998) "Early nonsurgical removal of chemically injured tissue enhances wound healing in partial thickness burns;" Burns 24(2): 166-172.
Houck et al., (1983) "Isolation of an Effective Debriding agent from the Stems of Pineapple Plants;" Int J Tissue Reac V(2): 125-134.
Pavan et al., (2012) "Properties and Therapeutic Application of Bromelain: A Review;" Biotechnology Research International, vol. 2012: 976203; 6 pages.
Perlstein et al., (1973) "Isolation and Characterization of a Protease Inhibitor from Commercial Stem Bromelain Acetone Powder;" J Supramol Struct 1(3): 249-254.
Rosenberg et al., (2004) "Safety and efficacy of a proteolytic enzyme for enzymatic burn debridement: a preliminary report;" Burns 30(8): 843-850.
Botanical Formulations, "What Does QS Mean;" Jan. 20, 2016, pp. 1-3.
Calbiochem, "Buffers. A guide for the preparation and use of the buffers in biological systems;" 2006, pp. 1-38.
European Medicines Agency; NexoBrid: "Concentrate of proteolytic enzymes enriched in bromelain;" 2012, pp. 1-126.
NCBI printout for cysteine proteinase precursor, AN11 [Ananas Comosus], CAA08861, downloaded from http://www.ncbi.nlm.nih.gov/protein/caa08861 on May 16, 2011; 2 pages.
Webpage for http://www.merriam-webster.com/dictionary/plurality downloaded Dec. 8, 2010; 5 pages.
International Search Report and Written Opinion, Appl. No. PCT/IL2017/050107 dated May 28, 2017.

* cited by examiner

Before treatment

After 11 treatments

Before treatment

After 11 treatments

DEBRIDING COMPOSITION FOR TREATING WOUNDS

This application is a 371 filing of International patent application no. PCT/IL2017/050107 filed Jan. 30, 2017, which claims the benefit of U.S. application No. 62/289,246 filed Jan. 31, 2016.

FIELD OF THE INVENTION

The present invention relates to debriding compositions. Particularly, the present invention relates to debriding compositions comprising a proteolytic enzyme mixture obtained from bromelain being in a dry form, and an aqueous gel carrier, wherein, prior to use, the proteolytic enzyme mixture being admixed with the aqueous gel carrier to form a debriding composition useful for debridement and treatment of chronic wounds.

BACKGROUND OF THE INVENTION

Chronic or hard to heal wounds are a common ailment, afflicting millions of people annually. The majority of chronic wounds are caused by a local or generalized vascular insufficiency that reduces blood flow to the skin and subcutaneous tissue. The most common type of chronic or hard to heal wounds include: pressure ulcers (decubiti or "bed sores"), diabetic ulcers, arterial ulcers, venous ulcers, and post surgical/post trauma ulcers.

Chronic wounds result in a severe damage to the skin. This damage may involve the entire thickness of the skin and may often include deeper tissues. The damaged skin loses the anatomic organization of a healthy skin, the stratum corneum is at least partially destroyed and consequently the inner layers of the skin are no longer protected from the external environment. Moreover, the damaged skin typically contains eschar, diseased and/or abnormal cells that must be removed in order to enable healing. Leaving the eschar in place extends and deepens the damage into the neighboring, undamaged tissues. This eschar also serves as a medium for bacteria growth and a source of infection, contamination and sepsis which may be life threatening.

Removal of the eschar, diseased and/or abnormal cells, also known as "debridement", is performed by surgical procedures, by mechanical means (dressings changes, bathing), by autolytic procedures (dressings that promote maceration) or by enzymatic means. Surgery is one of the most common procedures of debridement wherein small necrotic areas are excised of the entire damaged skin. This method is limited to small non-tangential surfaces. It also involves the removal of large fractions of healthy tissue which, if preserved, can serve as a source for the natural, spontaneous healing processes. Surgical procedures are also more expensive and require medical resources.

Enzymatic debridement is advantageous over mechanical and surgical debridement mainly since it is less painful, more selective and does not require the assistance of well-trained medical personnel. The application of proteolytic enzymes for debridement is well known in the art. These enzymes include those isolated from bacteria and those generally found in plant sources, such as papaya (papain), fig (ficin), and pineapple (bromelain). Hydrolytic enzymes derived from the pineapple plant that are useful for digestion, dissection and separation of non-viable, especially eschar tissue, from viable tissue in a mammalian host are described in U.S. Pat. Nos. 4,197,291; 4,226,854; 4,307,081; 4,329,430 and 5,830,739, among others.

The degree of the therapeutic activity obtained from topical application of proteolytic enzymes is governed, inter alia, by the intrinsic catalytic characteristics of the enzymes. The major problems associated with topical use of compositions comprising proteolytic enzymes are that the catalytic activity of the enzymes is rapidly attenuated due to the typical low pH at the lesion area, adsorption of the enzyme molecules to the surface of the wound bed and/or the surface of the dressing, and inhibition of enzymatic activity by moieties within the wound exudates. Therefore, obtaining stable enzymatic formulations is complicated.

Several ointments are currently being marketed for debriding eschar. These ointments are typically applied daily for several months to achieve the desired wound debridement.

U.S. Pat. No. 4,668,228 to Bolton et al., discloses debriding tapes which contain a proteolytic enzyme useful for debridement of eschar and necrotic tissue, e.g., subtilisin, bromelain, in dry powdered form on the adhesive mass surface of an occlusive or semi-occlusive surgical adhesive tape. According to U.S. Pat. No. 4,668,228, when the debriding tape is applied to a burned surface, water from the wound which cannot penetrate the occlusive tape backing activates the debriding enzymes.

U.S. Pat. No. 4,784,653 to Bolton et al., discloses an absorbent adhesive dressing for use in treating wounds of the ulcer and burn type which comprises a three layer sandwich-type constructions having an occlusive film as the outer layer, an absorbent layer of fibers as the middle layer, and a wet-stick adhesive as the inner wound facing adhesive layer which is made of an acrylic polymer having both hydrophilic and hydrophobic characteristics. According to U.S. Pat. No. 4,784,653, a debriding enzyme may be added to the adhesive mass, if desired.

U.S. Pat. No. 5,514,370 to Stern et al., discloses pharmaceutical compositions for topical application containing high concentrations of collagenase in non-aqueous excipients. U.S. Pat. No. 5,514,370 further discloses a method of treating a wound which comprises applying thereto a composition consisting essentially of a non-aqueous excipient and collagenase.

U.S. Pat. No. 5,804,213 to Rolf discloses a prepackaged dressing which includes dry particulate solids for forming a pourable, water-based natural or synthetic hydrocolloidal polymeric gel to dress wounds. According to U.S. Pat. No. 5,804,213, one dry constituent is the hydrocolloid which is contained in a compartment of a sealed container separate from moisture. After mixing with water, the admixture is sufficiently fluid to allow it to be poured or spread into a wound. Following application to the wound, the hydrated hydrocolloidal dispersion begins to solidify to form a solid, self-supporting flexible dressing which consists of water, hydrocolloid and a biologically active constituent.

U.S. Pat. No. 6,548,556 to Hobson et al. discloses an enzymatic anhydrous hydrophilic debrider that uses in combination a proteolytic enzyme and an anhydrous hydrophilic Poloxamer carrier.

U.S. Pat. No. 8,062,661 to Caldwell et al. discloses methods of debriding a skin wound which include contacting the skin wound with a hydrogel patch debridement composition and removing the hydrogel patch debridement composition from said skin wound to remove foreign matter from the skin wound.

International Application Publication No. WO 2006/054309 assigned to the applicant of the present invention discloses a debriding composition obtained from bromelain useful in debriding eschar tissues and in wound healing.

International Application Publication No. WO 2013/011514 assigned to the applicant of the present invention discloses a proteolytic extract obtained from bromelain for the treatment of connective tissue diseases which are associated with excess of collagen deposition, including Dupuytren's disease and Peyronie's disease.

There is a long-felt and unmet need for enzymatic debriding compositions which provide improved debridement of wounds and particularly of chronic wounds.

SUMMARY OF THE INVENTION

The present invention provides a debriding composition comprising: a mixture of proteolytic enzymes obtained from bromelain being in a dry form, a pH adjusting agent, and an aqueous gel carrier, wherein, prior to use, the mixture of the proteolytic enzymes being admixed with the pH adjusting agent and the aqueous gel carrier to form a debriding composition in the form of a gel having a certain viscosity and a certain pH. The present invention further provides methods for debridement of wounds, particularly of chronic wounds, comprising a step of applying the debriding composition of the present invention onto the wound site, thereby achieving wound debridement.

Wound debridement is a key process of wound bed preparation (WBP) and is considered an essential intervention in chronic wound management which may promote wound healing and complete wound closure.

It is known that the enzymatic debridement agents available today for the treatment of chronic wounds, such as Santyl® Ointment, are applied daily for long periods of time, e.g., for three, six or even twelve months, to achieve eschar removal.

It was previously shown by the applicant of the present invention that a gel formulation comprising: a proteolytic enzyme mixture obtained from bromelain in an amount of 10% (w/w), Carbopol® 980NF in an amount of 2.2% (w/w), dibasic sodium phosphate and water, was effective in burn wound debridement after a single 4 hour application. Due to the content of Carbopol® 980NF, that gel formulation had a high viscosity ranging from 55,000 centipoise (cP) up to 120,000 Cp.

It is now disclosed for the first time that aqueous gel formulations having a viscosity ranging from about 10,000 centipoise (cP) to about 45,000 cP which comprise: (i) a proteolytic enzyme mixture obtained from bromelain, designated herein API, in an amount of 1% (w/w) to 5% (w/w) of the total weight of the carrier; (ii) a pH adjusting agent; and (iii) a carrier comprising a cross-linked polymer of acrylic acid, a polar co-solvent, and water; such gel formulations enabled the penetration of the API to the eschar tissue of chronic wounds so as to effectively debride the non-viable tissue. The gel formulations of the present invention enabled eschar debridement of chronic wounds within few days, and as such are highly useful as a rapid and effective enzymatic debridement agent, particularly for chronic or hard to heal wounds.

It is further disclosed that the efficacy of the aqueous gel formulations of the present invention to debride chronic wounds in human subjects was demonstrated in chronic wounds of various etiologies, such as venous leg ulcers, diabetic lower extremity ulcers and traumatic/post surgery wounds. Yet, higher efficacy was unexpectedly demonstrated in the debridement of venous leg ulcers and diabetic lower extremity ulcers.

It is now disclosed that application of the aqueous gel formulations of the present invention on chronic wounds of human subjects for 4 hours/day for up to 10 consecutive days resulted in complete eschar/slough removal with mild or moderate adverse effects which were essentially similar to those observed with aqueous gel formulations devoid of the API, i.e., the gel vehicle. The adverse effects were transient and the patients recovered within few days. Thus, the aqueous gel formulations of the present invention are safe and well-tolerated.

It is now further disclosed that lower amounts of API in the aqueous gel formulations of the present invention can achieve effective eschar debridement if applied to the chronic wound for a longer duration per each application. Thus, the present invention discloses that 5% (w/w) of API in the aqueous gel formulations or even lower amounts of API, e.g., 2% (w/w) or even 1% (w/w), can be applied to a chronic wound for 24 hours, 48 hours, or even for longer periods of time per each application during a treatment period of 1-4 weeks, so as to achieve complete wound debridement.

It is further disclosed that the polar co-solvent glycerol added to the aqueous gel formulations of the present invention reduced skin irritation. The aqueous gel formulations of the present invention therefore comprise a polar co-solvent, preferably glycerol.

The aqueous gel formulations of the present invention have in some embodiments a pH ranging from about 6.5 to about 8.0, e.g., a pH of about 7.0. At this pH range, the activity of the proteolytic enzymes is essentially maximal. In order to achieve these pHs, the aqueous gel formulations of the present invention comprise a pH adjusting agent, thus enabling obtaining a highly efficacious enzymatic debriding agent.

Thus, the aqueous gel formulations of the present invention, also denoted throughout the specification and claims "debriding compositions", are highly advantageous as a rapid, efficacious, safe, and well-tolerated enzymatic agent for the debridement and treatment of wounds, and particularly of chronic or hard to heal wounds.

According to a first aspect, the present invention provides a debriding composition comprising:
  (a) a proteolytic enzyme mixture obtained from bromelain comprising stem bromelain (EC 3.4.22.32) and ananain (EC 3.4.22.31), the proteolytic enzyme mixture being in a dry or lyophilized form;
  (b) a pH adjusting agent; and
  (c) a carrier comprising:
    (i) a cross-linked polymer of acrylic acid;
    (ii) a polar co-solvent; and
    (iii) water,
wherein, prior to use, the proteolytic enzyme mixture being admixed with the pH adjusting agent and the carrier to form a debriding composition in the form of a gel characterized by having a viscosity in the range of about 10,000 centipoise (cP) to about 45,000 cP, and a pH ranging from about 6.0 to about 8.0, and wherein said proteolytic enzyme mixture is present in the debriding composition in an amount ranging from about 1% (w/w) to about 7% (w/w) of the total weight of the carrier.

According to some embodiments, the proteolytic enzyme mixture is present in the debriding composition in an amount ranging from about 2% (w/w) to about 7% (w/w) of the total weight of the carrier, such as in an amount of about 2%, 2.5%, 3%, 3.5%, 4%, 5%, 6% or about 7% (w/w) of the total weight of the carrier. Each possibility represents a separate embodiment of the invention. According to additional embodiments, the proteolytic enzyme mixture is present in the debriding composition in an amount ranging from about 1% (w/w) to about 5% (w/w). According to one exemplary embodiment, the proteolytic mixture is present in an amount of about 2.5% (w/w) of the total weight of the carrier. According to another exemplary embodiment, the proteolytic mixture is present in the debriding composition in an amount of 5% (w/w) of the total weight of the carrier.

According to additional embodiments, the pH adjusting agent is selected from the group consisting of sodium phosphate, sodium carbonate, potassium phosphate, and potassium carbonate. According to one embodiment, the pH adjusting agent is present in a dry form together with the proteolytic enzyme mixture. According to another embodiment, the pH adjusting agent is present together with the carrier. According to an exemplary embodiment, the pH adjusting agent is sodium phosphate. According to one embodiment, the sodium phosphate is anhydrous di-sodium hydrogen phosphate. According to additional embodiments, anhydrous di-sodium hydrogen phosphate is present in an amount ranging from about 0.1% (w/w) to about 2% (w/w) of the total weight of the carrier. According to a certain embodiment, anhydrous di-sodium hydrogen phosphate is present in an amount of about 0.25% (w/w) of the total weight of the carrier.

According to further embodiments, the cross-linked polymer of acrylic acid is a carbomer. According to yet further embodiments, the carbomer is selected from the group consisting of polymers of acrylic acid cross-linked with allyl sucrose or allyl pentaerythritol, polymers of acrylic acid and $C_{10}$-$C_{30}$ alkyl acrylate cross-linked with allyl pentaerythritol, carbomer homopolymers or copolymers that contain a block copolymer of polyethylene glycol and long chain alkyl acid ester, and a combination thereof. Each possibility represents a separate embodiment of the invention.

According to still further embodiments, the carbomer is selected from the group consisting of CARBOPOL® homopolymers, CARBOPOL® copolymers, CARBOPOL® interpolymers, and the like. Each possibility represents a separate embodiment of the invention.

According to further embodiments, the carbomers include, but are not limited to, CARBOPOL® 980 NF, CARBOPOL® 71 G NF, CARBOPOL® 971P NF, CARBOPOL® 974P NF, CARBOPOL® 981 NF, PEMULEN™ TR-1 NF, PEMULEN™ TR-2 NF, CARBOPOL® ETD 2020 NF, CARBOPOL® Ultrez 10 NF, carbomer 934 (CARBOPOL® 934 NF), carbomer 934P (CARBOPOL® 934P NF), carbomer 940 (CARBOPOL® 940 NF), carbomer 941 (CARBOPOL® 941 NF) and carbomer 1342 (CARBOPOL® 1342P NF). Each possibility represents a separate embodiment of the invention. According to some embodiments, the carbomer is Carbopol® 980 NF present in an amount ranging from about 0.5% (w/w) to about 1.5% (w/w) of the total weight of the carrier. According to a certain embodiment, Carbopol® 980 NF is present in an amount of about 1% (w/w) of the total weight of the carrier.

According to yet further embodiments, the polar co-solvent is selected from the group consisting of glycerol, polyethylene glycol (PEG), polypropylene glycol, polyglycerol, propylene glycol, ethanol, isopropyl alcohol, and a combination thereof. According to further embodiments, the polar c-solvent is glycerol present in an amount ranging from about 2% (w/w) to about 15% (w/w) of the total weight of the carrier. According to one exemplary embodiment, glycerol is present in an amount of 10% (w/w) of the total weight of the carrier.

According to still further embodiments, the viscosity of the debriding composition ranges from about 10,000 cP to about 30,000 cP, alternatively from about 15,000 cP to about 25,000 cP. Each possibility represents a separate embodiment of the invention. According to certain embodiments, the viscosity ranges from about 16,000 cP to about 22,000 cP.

According to yet further embodiments, the pH of the debriding composition ranges from about 6.0 to about 7.0, alternatively the pH is of about 7.0.

According to some embodiments, the debriding composition comprising:
(a) a proteolytic enzyme mixture obtained from bromelain comprising stem bromelain (EC 3.4.22.32) and ananain (EC 3.4.22.31) in an amount ranging from about 1% (w/w) to about 7% (w/w) of the total weight of the carrier;
(b) a pH adjusting agent;
(c) a carrier comprising:
   (i) a polymer of acrylic acid cross-linked with allyl sucrose or allyl pentaerythritol;
   (ii) glycerol; and
   (iii) water.

According to additional embodiments, the debriding composition comprising:
(a) a proteolytic enzyme mixture obtained from bromelain comprising stem bromelain (EC 3.4.22.32) and ananain (EC 3.4.22.31) in an amount ranging from about 1% (w/w) to about 7% (w/w) of the total weight of carrier;
(b) a pH adjusting agent;
(c) a carrier comprising:
   (i) Carbopol® 980 NF in an amount ranging from about 0.5% to about 1.5% (w/w) of the total weight of the carrier;
   (ii) glycerol; and
   (iii) water.

According to further embodiments, the debriding composition comprising:
(a) a proteolytic enzyme mixture obtained from bromelain comprising stem bromelain (EC 3.4.22.32) and ananain (EC 3.4.22.31) present in a first container in an amount of ranging from about 1% to about 7% (w/w), preferably in an amount ranging from about 1% (w/w) to about 5% (w/w) of the total weight of the carrier;
(b) a carrier present in a second container comprising:
   (i) Carbopol® 980 NF in an amount of about 0.9% (w/w) of the total weight of the carrier;
   (ii) glycerol in an amount of about 10% (w/w) of the total weight of the carrier;
   (iii) anhydrous di-sodium hydrogen phosphate present in an amount of about 0.25% (w/w) of the total weight of the carrier; and
   (iv) water,
wherein the viscosity of the debriding composition ranges from about 15,000 cP to about 25,000 cP and the pH ranges from about 6.0 to about 7.0.

According to another aspect, the present invention provides a method for debridement of a wound comprising a step of applying to the wound site of a subject in need of such treatment a therapeutically effective amount of the debriding composition according to the principles of the present invention.

According to some embodiments, the method comprising the step of applying to the wound site the debriding composition of the present invention, said debriding composition comprises:
(a) a proteolytic enzyme mixture obtained from bromelain comprising stem bromelain (EC 3.4.22.32) and ananain (EC 3.4.22.31) present in a dry or lyophilized form;

(b) a pH adjusting agent;
(c) a carrier comprising:
   (i) a cross-linked polymer of acrylic acid;
   (ii) a polar co-solvent; and
   (iii) water.
wherein, prior to use, the proteolytic enzyme mixture is admixed with the pH adjusting agent and the carrier to form a debriding composition in the form of a gel characterized by having a viscosity in the range of about 10,000 centipoise (cP) to about 45,000 cP, and a pH ranging from about 6.0 to about 8.0, and wherein said proteolytic enzyme mixture is present in the debriding composition in an amount ranging from about 1% (w/w) to about 7% (w/w) of the carrier.

According to some embodiments, the method comprising a step of applying the debriding composition which comprises:
   (a) a proteolytic enzyme mixture obtained from bromelain comprising stem bromelain (EC 3.4.22.32) and ananain (EC 3.4.22.31) present in a dry or lyophilized form in a first container in an amount ranging from about 1% (w/w) to about 7% (w/w), preferably in an amount ranging from about 1% (w/w) to about 5% (w/w) of the carrier;
   (b) a carrier present in a second container comprising:
      (i) Carbopol® 980 NF in an amount of about 0.9% (w/w) of the total weight of the carrier;
      (ii) glycerol in an amount of about 10% (w/w) of the total weight of the carrier;
      (iii) anhydrous di-sodium hydrogen phosphate in an amount of about 0.25% (w/w); and
      (iv) water.
wherein the viscosity of the composition ranges from about 15,000 cP to about 25,000 cP and the pH ranges from about 6.0 to about 7.0.

According to additional embodiments, the wound to be debrided by the debriding composition of the present invention is a hard to heal or chronic wound. According to further embodiments, the hard to heal or chronic wound is selected from the group consisting of a diabetic ulcer, a venous stasis ulcer, an arterial insufficiency ulcer, a pressure ulcer, a post-operative and a post trauma wound. Each possibility represents a separate embodiment of the invention. According to further embodiments, the hard to heal or chronic wound is selected from the group consisting of a diabetic lower extremity ulcer, a venous leg ulcer, a post-operative wound, and a post trauma wound. Each possibility represents a separate embodiment of the invention. According to certain embodiments, the hard to heal or chronic wound is a diabetic lower extremity ulcer or a venous leg ulcer.

According to further embodiments, the debriding composition for treating a hard to heal or chronic wound is applied to the wound site in a regimen of at least one application, wherein the debriding composition is maintained in contact with the wound site for about 4-24 hours per application. According to yet further embodiments, the debriding composition is applied to the wound site in a regimen of at least 2, 3, 4, 5, 6, 7, 8, 9, or at least 10 applications, or until eschar is debrided, wherein the debriding composition is maintained in contact with the wound site for about 4-24 hours per application. Each possibility represents a separate embodiment of the invention. According to one exemplary embodiment, the debriding composition is applied in a regimen of 10 applications, wherein the debriding composition is maintained in contact with the wound site for about 4 hours per application.

According to still further embodiments, the debriding composition is applied to the wound site in a regimen of at least one application, wherein the debriding composition is maintained in contact with the wound site for about 24 hours per application. According to yet further embodiments, the debriding composition is applied to the wound site in a regimen of at least 2, 3, 4, 5, 6, 7, 8, 9, or at least 10 applications, or until eschar is debrided, wherein the debriding composition is maintained in contact with the wound site for about 24 hours per application. Each possibility represents a separate embodiment of the invention. According to one exemplary embodiment, the debriding composition is applied in a regimen of 10 applications, wherein the debriding composition is maintained in contact with the wound site for about 24 hours per application.

According to additional embodiments, the debriding composition is applied to the wound site in a regimen of at least one application, wherein the debriding composition is maintained in contact with the wound site for about 48 or for about 72 hours or for any integer in between per application. According to further embodiments, the debriding composition is applied to the wound site in a regimen of at least 2, 3, 4, 5, 6, 7, 8, 9, or at least 10 applications, or until eschar is debrided, wherein the debriding composition is maintained in contact with the wound site for about 48 hours or for about 48 hours or for any integer in between per application. Each possibility represents a separate embodiment of the invention. According to one exemplary embodiment, the debriding composition is applied in a regimen of 10 applications, wherein the debriding composition is maintained in contact with the wound site for about 48 hours per application.

According to yet further embodiments, the debriding composition is applied to a chronic wound in a regimen of three times a week for at least one week, wherein said debriding composition is maintained in contact with the wound site for a duration selected from the group consisting of 48 hours per application and 72 hours per application. According still further embodiments, the debriding composition is applied to a chronic wound in a regimen of three times a week for at least 4, 5, 6, 7, 8, 9, or at least 10 applications, or until eschar is debrided, wherein said debriding composition is maintained in contact with the wound site for a duration selected from the group consisting of 48 hours per application and 72 hours per application. Each possibility represents a separate embodiment of the invention. According to one exemplary embodiment, the debriding composition is applied three times a week in a regimen of 10 applications.

According to still further embodiments, the regimen is repeated one, two, three, or more times or until eschar is completely debrided and/or wound closure is obtained. It is to be noted that if the treatment regimen is repeated, the treatment can be continuous or can be one or more days, one or more weeks, or one or more months apart from each other. Additionally or alternatively, if eschar reoccurs and wound closure is not yet obtained, the regimen is repeated one, two, or more times until eschar is completely debrided and/or wound closure is obtained.

According to yet further embodiments, the method further comprises a step of administering to the subject an active agent selected from the group consisting of anesthetic agents, antibacterial agents, antifungal agents, and anti-inflammatory agents. The active agent, such as, for example, an anesthetic agent, can be topically applied to the wound site or can be administered orally or parenterally before application of the debriding formulation, concomitant with the application of the debriding formulation or after application of the debriding formulation.

According to another aspect, the present invention provides a method of treating a wound comprising a step, as defined herein above, of applying to the wound site of a subject in need of such treatment a therapeutically effective amount of the debriding composition according to the principles of the present invention. According to a certain embodiment, the wound is a hard to heal or chronic wound.

According to a further aspect, the present invention provides a method for wound healing or wound closure comprising a step, as defined herein above, of applying to the wound site of a subject in need of such treatment a therapeutically effective amount of the debriding composition according to the principles of the present invention. According to a certain embodiment, the wound is a hard to heal or chronic wound.

According to another aspect, the present invention provides a debriding composition according to the principles of the present invention for use in a method of debridement of a wound and/or in treating a wound and/or in wound healing and/or in wound closure as defined herein above. According to a certain embodiment, the wound is a hard to heal or chronic wound.

These and other embodiments of the present invention will be better understood in relation to the figures, description, examples and claims that follow.

BRIEF DESCRIPTION OF THE FIGURES

FIG. 1A shows a chronic wound before treatment and FIG. 1B shows a chronic wound after eleven treatments with EscharEx Gel 3%. As a control, a chronic wound induced in a pig (FIG. 1C) was treated with Gel Vehicle for eleven treatments (FIG. 1D).

DETAILED DESCRIPTION OF THE INVENTION

Figure 1A:
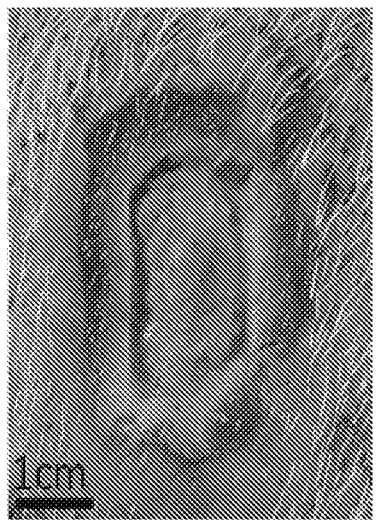
FIGS. 1A-D are micrographs of a chronic wound induced in a pig.

The present invention provides a debriding composition which comprises: (i) a proteolytic enzyme mixture obtained from bromelain present in a dry or lyophilized form; (ii) a pH adjusting agent; and (iii) a carrier comprising a cross-linked polymer of acrylic acid, a polar co-solvent, and water, wherein prior to use, the proteolytic enzyme mixture being admixed with the pH adjusting agent and the carrier to form a debriding composition in the form of a gel having a viscosity in the range of about 10,000 cP to about 45,000 cP and a pH in the range of about 6.0 to about 8.0.

The term "proteolytic enzyme mixture obtained from bromelain" as used throughout the specification and claims refers to an enzymatic preparation partially purified from bromelain.

The term "bromelain" refers to a protein extract derived from the stems of pineapple plants which can be purchased commercially.

The proteolytic enzyme mixture obtained from bromelain (also termed Debrase® or NexoBrid®) and the preparation thereof are disclosed in WO 2006/054309 and WO 2013/011514, the content of which is incorporated by reference as if fully set forth herein. The proteolytic enzyme mixture obtained from bromelain comprises at least two of the cysteine proteases present in bromelain: stem bromelain (EC 3.4.22.32) and ananain (EC 3.4.22.31). The proteolytic mixture can further comprise one or more of the cysteine protease precursors of bromelain such as, for example, ananain (EC 3.4.22.31) precursor, fruit bromelain (EC 3.4.22.33) precursor, and stem bromelain (EC 3.4.22.31) precursor. The proteolytic mixture can further comprise cysteine protease fragments, a jacalin-like lectin, and/or bromelain inhibitors (see, for example, WO 2006/054309). According to a certain embodiment, the proteolytic mixture obtained from bromelain comprises stem bromelain (EC 3.4.22.32), ananain (EC 3.4.22.31), a cysteine protease precursor of bromelain, and optionally a jacalin-like lectin.

The proteolytic mixture can be obtained by the procedure disclosed in WO 2013/011514. As the last step of the preparation, the proteolytic mixture is lyophilized and stored as a lyophilized powder until use. The proteolytic enzyme mixture is highly stable as a lyophilized or dried powder and can be stored at 2-8° C. for 3 years. After this period of time, the proteolytic enzyme mixture maintains at least 90% of the original enzymatic activity as determined at the end of the production process.

The terms "dry", "lyophilized" or "anhydrous" as used interchangeably throughout the specification and claims refer to the proteolytic enzyme mixture or to the pH adjusting agent which contain water in an amount of up to 3% (w/w) of the total weight of the mixture or of the pH adjusting agent, alternatively water is present in an amount of up to 2%, 1%, 0.5%, or further alternatively of up to 0.1% (w/w) of the total weight of the mixture or of the pH adjusting agent. Each possibility represents a separate embodiment of the invention. According to a certain embodiment, the proteolytic mixture and the pH adjusting agent are devoid of water.

The cross-linked polymer of acrylic acid useful for practicing the present invention is a carbomer. Suitable carbomers include, but are not limited to, the various polymers sold under the trade name CARBOPOL® by Lubrizol Advanced Materials, Cleveland, Ohio, including, for example, CARBOPOL® homopolymers (polymers of acrylic acid cross-linked with allyl sucrose or allyl pentaerythritol) such as CARBOPOL® 71 G NF, CARBOPOL® 971P NF, CARBOPOL® 974P NF, CARBOPOL® 980 NF, and CARBOPOL® 981 NF; CARBOPOL® copolymers (polymers of acrylic acid and $C_{10}$-$C_{30}$ alkyl acrylate cross-linked with allyl pentaerythritol) such as PEMULEN™ TR-1 NF and PEMULEN™ TR-2 NF; CARBOPOL® interpolymers (carbomer homopolymers or copolymers that contain a block copolymer of polyethylene glycol and long chain alkyl acid ester) such as CARBOPOL® ETD 2020 NF and CARBOPOL® Ultrez 10 NF; "traditional" carbomers such as carbomer 934 (CARBOPOL® 934 NF), carbomer 934P (CARBOPOL® 934P NF), carbomer 940 (CARBOPOL® 940 NF), carbomer 941 (CARBOPOL® 941 NF) and carbomer 1342 (CARBOPOL® 1342P NF). Each possibility represents a separate embodiment of the invention.

The polar co-solvents include, but are not limited to, glycerol, polyethylene glycol (PEG), polypropylene glycol, polyglycerol, propylene glycol, ethanol, sorbitol, isopropyl alcohol, and a combination thereof. Each possibility represents a separate embodiment of the invention. According to a certain embodiment, the polar co-solvent is glycerol.

The term "pharmaceutically acceptable" means approved by a regulatory agency of the Federal or a state government or listed in the U. S. Pharmacopeia or other generally recognized pharmacopeia for use in humans. The constituents of the debriding composition of the present invention are all pharmaceutically acceptable agents.

The term "about" refers to a value which is 10% above or below the indicated value.

The debriding composition can further comprise a preservative such as, for example, benzyl alcohol, parabens, methyl- or propylhydroxybenzoates and a combination thereof and/or an anti-oxidant such as, for example, ascorbic acid, dihydroquinon, butylated hydroxytoluene, dithiothreitol, and a combination thereof and/or an anti-aggregation agent such as, for example, an oligosaccharide, e.g., lactose and the like.

The debriding composition can further comprise an active agent such as an anesthetic agent, an antibacterial agent, an antifungal agent, an anti-inflammatory agent, an analgesic agent, a growth factor, an agent promoting healing or a combination thereof. The anesthetic agents include, but are not limited to, amethocaine (tetracaine), lignocaine (lidocaine), xylocaine, bupivacaine, prilocaine, ropivacaine, benzocaine, mepivocaine, cocaine, and a combination thereof.

The antibacterial agents include, but are not limited to, amanfadine hydrochloride, amanfadine sulfate, amikacin, amikacin sulfate, amoglycosides, amoxicillin, ampicillin, amsamycins, bacitracin, beta-lactams, candicidin, capreomycin, carbenicillin, cephalexin, cephaloridine, cephalothin, cefazolin, cephapirin, cephradine, cephaloglycin, chilomphenicols, chlorhexidine, chlorhexidine gluconate, chlorhexidine hydrochloride, chloroxine, chlorquiraldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erhmycin stearate, farnesol, floxacillin, gentamicin, gentamicin sulfate, gramicidin, giseofulvin, haloprogin, haloquinol, hexachlorophene, iminocylcline, iodochlorhydroxyquin, kanamycin, kanamycin sulfate, lincomycin, lineomycin, lineomycin hydrochloride, macrolides, meclocycline, methacycline, methacycline hydrochloride, methenine, methenamine hippurate, methenamine mandelate, methicillin, metonidazole, miconazole, miconazole hydrochloride, minocycline, minocycline hydrochloride, mupirocin, nafcillin, neomycin, neomycin sulfate, netimicin, netilmicin sulfate, nitrofurazone, norfloxacin, nystatin, octopirox, oleandomycin, orcephalosporins, oxacillin, oxyteacline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones such as fluoroquinolones, streptomycin sulfate, tetracycline, tobramycin, tolnaftate, triclosan, trifampin, rifamycin, rolitetracycline, silver salts, spectinomycin, spiramycin, struptomycin, sulfonamide, tetracyclines, tetracycline, tobramycin, tobramycin sulfate, triclocarbon, triclosan, trimethoprim-sulfamethoxazole, tylosin, vancomycin, yrothricin, and a combination thereof. Each possibility represents a separate embodiment of the invention.

The antifungal agents include, but are not limited to, nystatin, clotrimazole, miconazole, ketoconazole, fluconazole, thiabendazole, econazole, clomidazole, isoconazole, tiabendazole, tioconazole, sulconazole, bifonazole, oxiconazole, fenticonazole, omoconazole, sertaconazole, flutrimazole, and a combination thereof. Each possibility represents a separate embodiment of the invention.

The anti-inflammatory agent can be non-steroidal, steroidal, or a combination thereof. Non limiting examples of non-steroidal anti-inflammatory agents include oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Each possibility represents a separate embodiment of the invention.

Non-limiting examples of steroidal anti-inflammatory drugs include corticosteroids such as hydrocortisone, hydroxyl-triamcinolone, alpha-methyl dexamethasone, dexamethasone phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocorisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, and triamcinolone. Each possibility represents a separate embodiment of the invention.

Analgesic agents include, but are not limited to, codeine, hydrocodone, oxycodone, fentanyl, and propoxyphene. Each possibility represents a separate embodiment.

Growth factors include, but are not limited to, epidermal growth factors, fibroblast growth factors, insulin-like growth factors, and the like.

Agents promoting healing include, but are not limited to, hyaluronic acid and the like.

According to a preferred embodiment, the debriding composition is sterile.

The viscosity of the gel formulations of the present invention can be measured by any known means. The viscosity can be determined by absolute viscosity measurements using cone plate geometry. Alternatively, a Brookfield (spindle and cup) viscometer can be used to calculate the viscosity of the gel formulations described herein. The viscosity ranges referred to herein are all measured at room temperature.

The proteolytic enzyme mixture and the carrier can be stored in a first compartment and a second compartment, respectively, of a single container or can be stored in two separate containers, namely in a first container and a second container. The pH adjusting agent can be anhydrous or dried and can be stored in the first compartment or container with the proteolytic enzyme mixture. Alternatively, the pH adjusting agent can be stored with the carrier in the second compartment or container. Alternatively, the pH adjusting agent can be stored in a third, distinct compartment or container. According to a certain embodiment, the pH adjusting agent is stored with the carrier in the second compartment or container, and prior to use, the proteolytic enzyme mixture and the carrier are admixed to form the debriding composition of the present invention.

According to another aspect, the present invention provides a system comprising three containers, wherein a first container comprises the proteolyic enzyme mixture, a second container comprises the carrier, and a third container comprises the pH adjusting agent. Alternatively, the system comprises two containers, wherein a first container comprises the proteolytic enzyme mixture and the second container comprises the carrier and the pH adjusting agent.

According to some embodiments, the composition is devoid of adhesive agents, and as such it is non-adhesive.

Uses of the Debriding Composition

The present invention provides a method for debridement of a skin wound comprising a step of topically applying a therapeutically effective amount of the debriding composition of the present invention to the skin wound site of a subject in need of such treatment, thereby debriding the eschar of the wound to promote wound healing and wound closure. According to certain embodiments, the wound is a chronic or hard to heal wound.

The present invention further provides a method of treating a skin wound comprising a step of topically applying a therapeutically effective amount of the debriding composition of the present invention to the skin wound site of a subject in need of such treatment, thereby treating the wound. According to certain embodiments, the wound is a chronic or hard to heal wound.

The terms "chronic wound", "chronic skin wound" or a "hard to heal wound" as used interchangeably throughout the specification and claims refer to a wound that has failed to proceed through an orderly and timely series of events to produce a durable structural, functional, and/or cosmetic closure as wounds do. Wounds that do not heal within one month are considered chronic or hard to heal wounds.

The term "debridement of a wound" as used herein refers to the removal of nonviable tissue: necrotic eschar, slough or fibrin, and bacteria/biofilm from a wound. Necrotic eschar is a thin or thick, leathery, devitalized, black, brown or tan tissue, whereas slough and biofilm are exudative, white or yellow-greenish mottled, tenuous tissue on the wound bed. Necrotic tissue, foreign material and bacteria impede the body's attempt to heal by producing or stimulating the production of metalloproteases that interfere with the local wound-healing process. This hostile environment allows bacteria to proliferate, further colonize the wound within the exudates, debris, and purulent discharges ("slough") that cover the wound bed. In addition, the bacteria secrete structural products that together with the slough form the biofilm, thus protect their colonies from potential destruction. The bacteria produce their own wound-inhibiting enzymes and, more significantly, consume much of the scarce, available local resources that are necessary for wound healing.

In chronic wounds several different factors may play an important role. Exposed surfaces such as bone, tendons, fascia or even fat do not support cellular proliferation and they dry and become foreign bodies such as synthetic implants. Any interference with local blood supply (arterial, venous, lymphatic, pressure etc.) may cause a wound to become hard to heal and chronic. Granulation tissue may become recalcitrant, atrophic, lose its rich vascular matrix, become darker and opaque in color and will not take any part in the wound healing and closure processes.

The term "wound bed preparation (WBP)" as used herein refers to a wound bed which results from a proper debridement in order to accelerate endogenous healing or to facilitate the effectiveness of other therapeutic measures. It is a process of debriding, removing various "burdens" within both the wound and the patient that impede healing. Burdens within the wound include exudate, bacteria, biofilm and necrotic/cellular debris. The overall health status of the patient is important to the healing process. In chronic wounds, removal of the offending eschar, slough or biofilm may result in a clean wound bed, yet such a wound bed may still be inadequate for future healing if the patient's systemic or the extremity's condition cannot support it.

A wound bed prepared for healing is one without eschar, slough, fibrin or biofilm that also has a viable bed of healthy tissues and/or healthy granulation tissue (level >7 in the granulometer scale) that will allow the wound to close spontaneously by scarring and contracture-epithelialization (optionally using modalities such as biological dressings, wound-healing enhancing dressings, synthetic wound dressings, vacuum or ozone wound healing systems) over the viable, clean bed or will support autologous STSG (Split Thickness Skin Graft) or skin allografting.

According to some embodiments, debridement of a wound refers to removal of at least 50%, alternatively of at least 75% of the non-viable tissue which is present prior to treatment. Each possibility is a separate embodiment of the invention. According to certain embodiments, debridement of a wound refers to removal of at least 90%, or at least 95%, and preferably of 100% of the non-viable tissue which is present prior to treatment; such debridement, namely of 90% or more of the non-viable tissue present prior to treatment, is referred throughout the specification and claims as "complete debridement of a wound".

The term "wound closure" refers to the process of regenerating the covering cell layers of a tissue. Thus, promoting wound closure means creating a positive effect in the regeneration of the covering cell layers. The positive effect can be an acceleration of the regeneration process or a decrease of the damaged area of the wound.

The term "therapeutically effective amount" is that amount of the proteolytic enzyme mixture which is sufficient to provide a beneficial effect to the subject to which the composition is administered.

According to some embodiments, the debriding composition of the present invention can be applied daily to the chronic wound site for about 4-24 hours, or for any integer in-between, for a treatment period of at least one day. Alternatively, the debriding composition of the present invention can be applied daily to the chronic wound site for about 4-24 hours, or for any integer in-between, for a treatment period of at least 2, 3, 4, 5, 6, 7, 8, 9, or 10 consecutive days or until the eschar is debrided. Each possibility is a separate embodiment of the invention.

According to additional embodiments, the debriding composition of the present invention can be applied to the chronic wound site in a regimen of at least one application, wherein the debriding composition is maintained in contact with the wound site for about 4-24 hours, such as for about 24 hours, per application. Alternatively, the debriding composition of the present invention can be applied to the chronic wound site in a regimen of at least 2, 3, 4, 5, 6, 7, 8, 9, or at least 10 applications or until the eschar is debrided, wherein the debriding composition is maintained in contact with wound site for about 4-24 hours, such as for about 24 hours, per application. Each possibility is a separate embodiment of the invention. According to one embodiment, the duration of the regimen is of at least one day. Alternatively, the duration of the regimen is up to four weeks, preferably of up to 10 applications of about 24 hours per application.

According to further embodiments, the debriding composition of the present invention can be maintained in contact with the chronic wound site for about 48 hours per application in a regimen of at least one application. Alternatively, the debriding composition of the present invention can be maintained in contact with the chronic wound site for about 48 hours per application in a regimen of at least 2, 3, 4, 5, 6, 7, 8, 9, or at least 10 applications or until the eschar is debrided. Each possibility is a separate embodiment of the invention. According to one embodiment, the duration of the regimen is of at least two days. Alternatively, the duration of the regimen is of up to four weeks, preferably of up to 10 applications of about 48 hours per application.

According to yet further embodiments, the debriding composition of the present invention can be maintained in contact with the chronic wound site for about 72 hours per application in a regimen of at least one application, such as of at least 2, 3, 4, 5, 6, 7, 8, 9, or at least 10 applications or until the eschar is debrided. Each possibility is a separate embodiment of the invention. According to one embodiment, the duration of the regimen is of at least three days. Alternatively, the duration of the regimen is up to four weeks, preferably of up to 10 applications of about 72 hours per application.

According to yet further embodiments, the treatment regimen can be repeated one, two, three, or more times until wound is completely debrided and/or wound closure is achieved. If repeated, the regimens can be continuous/sequential to each other or can be days, weeks or months apart from each other.

According to some embodiments, the methods of the present invention can further comprise a step of covering the debriding composition with an occlusive layer or dressing to maintain or hold the composition at the wound site.

According to some embodiments, the methods of the present invention can further comprise an additional step of washing the wound site at the end of the application/contact time, such as, for example, after 4 hours or after 24 hours or after 48 hours or after 72 hours of the application/contact time.

It is to be understood that ranges of numerical values indicated throughout the specification and claims include any integer in between.

According to some embodiments, if the wound site is washed and a subsequent application of the debriding composition is performed hours or days later, a wet or moist dressing layer, preferably moist saline gauze, can be applied on the wound site According to additional embodiments, the method of the present invention can further comprise a step of protecting the wound edges and the peri-wound skin during debridement.

The present invention encompasses combination therapy wherein the methods of the present invention can be combined with known debridement methods, such as, surgical or sharp debridement. According to some embodiments, the methods of the present invention can be performed prior to surgical or sharp debridement. Alternatively, the methods of the present invention can be performed after surgical or sharp debridement.

According to some embodiments, the therapeutically effective amount of API applied to a wound site ranges between about 0.1 gr to about 2 gr per 100 $cm^2$ of wound surface. According to additional embodiments, the amount of the debriding composition applied to a wound site is of about 20 gr per 100 $cm^2$ of wound surface.

Example 1

Toxicity Study of Gel Formulations

This study aimed at evaluating the dermal toxicity of two gel formulations. Both gel formulations were aqueous formulations which contained 0.9% Carbopol 980NF. However, only one of the formulations contained 10% glycerol. The gel formulations also contained a mixture of proteolytic enzymes obtained from bromelain in an amount of 2.5% or 5% w/w of the total weight of the gel formulation.

The proteolytic mixture obtained from bromelain, designated herein after API to denote the active pharmaceutical ingredient, also known as Debrase® or NexoBrid®, was prepared as previously described (see, for example, WO 2013/011514). Prior to treatment, API in an amount of 1 gr powder or 0.5 gr powder were mixed with 20 gr of a gel vehicle which contained the following constituents: 0.9% w/w Carbopol® 980NF with or without 10% w/w glycerol, 0.25% w/w di-sodium hydrogen phosphate anhydrous, and water. Prior to application onto a skin site, the gel vehicle and the Debrase® powder were mixed up to 15 minutes to form the gel formulation.

Crossbred domestic pigs were anesthetized with xylazine and ketamine HCl administered intramuscularly (i.m.), diazepam administered intravenously (i.v.), and inhalation of isoflurane 5% and oxygen. Hair on the back of the pigs was clipped and washed with an antibiotic soap and sterile iodine. The skin was dried with sterile gauze. To each skin site (3 cm×3 cm) 2 gr of each gel formulation were applied.

Each gel formulation was applied topically once a day for 4 hours on the back of the pig and the formulation was removed at the end of the treatment. The skin sites were photographed before and after application of the gel formulation and evaluated for erythema and edema using a Draize scale:

Erythema:
0—No erythema
1—Very slight erythema (barely perceptible)
2—Well-defined erythema
3—Moderate erythema
4—Severe erythema (beet redness) slight eschar formation (injuries in depth)

Edema:
0—No edema
1—Very slight edema
2—Slight edema (edges of area well defined by definite raising)
3—Moderate edema (raised approximately 1 millimeter)
4—Severe edema (raised more than 1 millimeter and extending beyond area of exposure).

The skin sites were also evaluated histopathologically. The skin sites were then dressed with elastic bandage until the next treatment. This procedure repeated for 14 consecutive days. Gel vehicle with or without glycerol were used as a control.

Results

The results indicated that erythema was first observed for both gel formulations, i.e., with without glycerol, after the $4^{th}$ treatment and the mean score values were 0.5 and 1.0 for 2.5% w/w and 5% w/w of API. The mean grade of erythema increased as the number of treatments increased and was present until day 14. Erythema was not observed in skin sites treated with the gel vehicle alone. The results also indicated that erythema increased as a function of the API amount in the gel formulation. The maximal average score of erythema caused by the gel formulation with glycerol which contained API in the amount of 5% w/w of the total weight of the gel formulation was 2.33 and the maximal average score of erythema caused by the gel formulation with glycerol that contained API in the amount of 2.5% w/w of the total weight of the gel formulation was 1.33. The maximal average score of erythema caused by the gel formulation without glycerol which contained API in the amount of 5% w/w of the total weight of the gel formulation was 2.66 and the maximal average score of erythema caused by the gel formulation without glycerol that contained API in the amount of 2.5% w/w of the total weight of the gel formulation was 2.0.

For both gel formulations only slight edema was observed (maximal score average 0.66).

Thus, these results demonstrate that higher amounts of API in the gel formulations bring about to a higher level of skin irritation and that glycerol reduced skin irritation. As a result, the subsequent experiments were performed using API mixed with the gel vehicle containing 10% glycerol, 0.9% w/w Carbopol® 980NF, 0.25% w/w di-sodium hydrogen phosphate anhydrous, and water; this gel formulation which contained the API and the gel vehicle was designated EX01 or EscharEx Gel.

Example 2

Effect of Application Duration and API Amount on Chronic Wound Treatment

This study aimed at determining the application duration and the amount of API in the gel formulation which are necessary to achieve maximal efficacy of eschar removal in chronic wounds.

A chronic wound model was established in crossbred domestic pigs. Four amounts of API (0, 0.75%, 1.25% and 5% w/w) were mixed with the gel vehicle containing glycerol as described in Example 1 herein above and were applied on a chronic wound for three application durations (1 hr, 4 hours and 24 hours) for 10 consecutive days. At the end of the ten day period, also denoted the "treatment period", the chronic wounds of the pigs were observed for additional 14 days, denoted "the recovery period", to evaluate the effect of debridement on the healing rate of chronic wounds.

The chronic wounds were photographed at the beginning and during the treatment period as well as during the recovery period. The eschar area and the wound area were evaluated visually, measured by ImageJ software (NIH, MD, USA) and analyzed by JMP® statistical software (SAS Inc., NC, USA). In each photograph, the wound size and eschar size were measured. Erythema and edema were evaluated as described in Example 1 herein above. Biopsies were obtained from the center and from the edge of each wound before the first treatment, after the last treatment, and at the end of the recovery period. The tissues were embedded in paraffin, sectioned and stained with Hematoxylin and Eosin (H&E).

The measurements from the photographs were used to calculate the following parameters ("/" means "out of"):

1) Percent eschar area/wound area, at the end of the period.

2) The area under the curve (AUC) where the x axis is the treatment number and y axis is the percent eschar. This parameter shows the efficacy of the treatment: the more effective a treatment is, the smaller the area under the curve.

3) Percent wound size/initial size, at the end of the period.

4) The area under the curve (AUC) where the x axis is treatment number and y axis is the percent wound size of initial size. This parameter shows the wound closure: the faster the wound closes, the smaller the area.

Results

At the beginning of the treatment period, the chronic wounds already developed eschar. FIGS. 1A and 1C are representative photographs showing the chronic wound before treatment. The eschar was composed of two distinct areas: the center of the wound where the skin was fully excised, and the wound edges. In the center, a thin eschar layer was developed, while in the edges, the eschar was composed of necrotic skin.

Figure 1B:
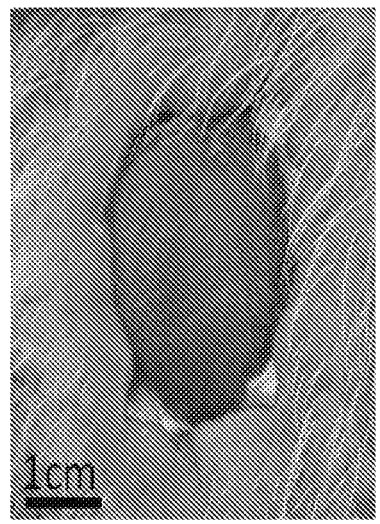
Figure 1C:
Figure 1D:
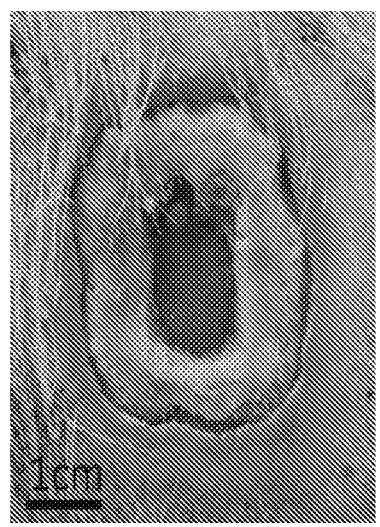

In chronic wounds treated with the gel formulation containing API (denoted EscharEx Gel or EX01), the eschar softened and gradually dissolved from treatment to treatment until the dissolution at the circumference caused the eschar to wholly disconnect from the viable tissue (FIG. 1B). In contrast, chronic wounds treated with the gel vehicle barely changed their appearance and consistency during the treatment period (FIG. 1D). In few cases, after the $10^{th}$ treatment, chunks of eschar were disconnected from the wound bed. In both the gel vehicle and the gel formulation EX01, if eschar remained after the last treatment, it dried out and fell off the wound during the recovery period.

The area surrounding the wound treated with the gel formulation EX01 developed edema and erythema during the treatment period despite the protection with Vaseline. This phenomenon of skin irritation was more pronounced in the 24 hr treatment group with 5% (w/w) API. The 24 hr treatment with 1.25% (w/w) API caused similar skin irritation as obtained by the 4 hr treatment with 5% (w/w) API in the gel formulation EX01. Both erythema and edema disappeared completely after 1-2 days during the recovery period.

Figure 2C:
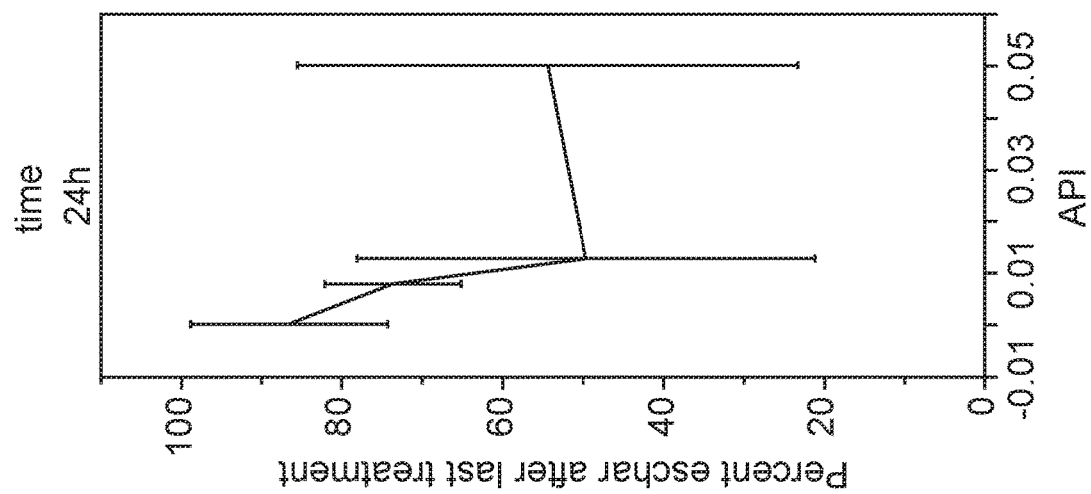
FIGS. 2A-C show the percent eschar after the $10^{th}$ treatment with the EsxharEx Gel as a function of the amount of the active pharmaceutical ingredient (API) applied to the wound for 1 hour (FIG. 2A), 4 hours (FIG. 2B) and 24 hours (FIG. 2C).
Figure 2B:
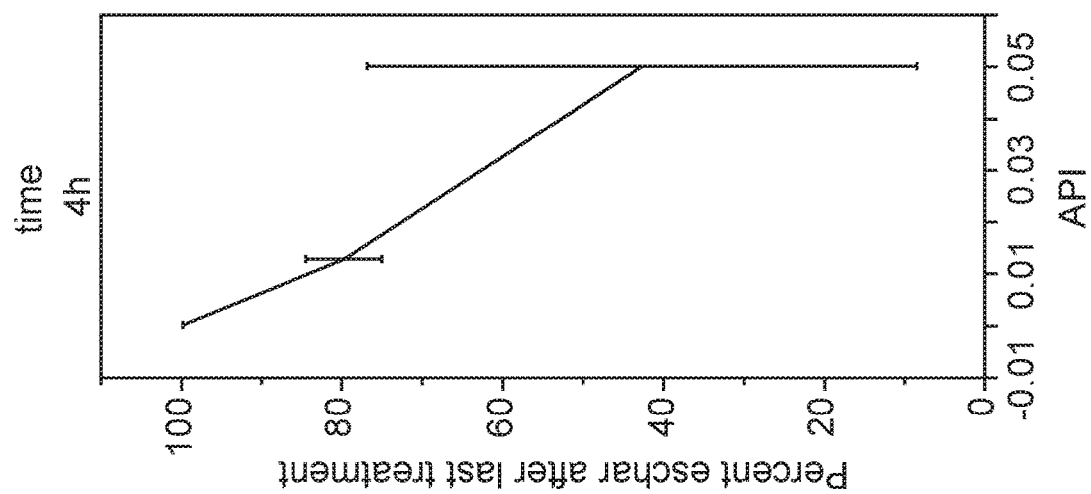
Figure 2A:
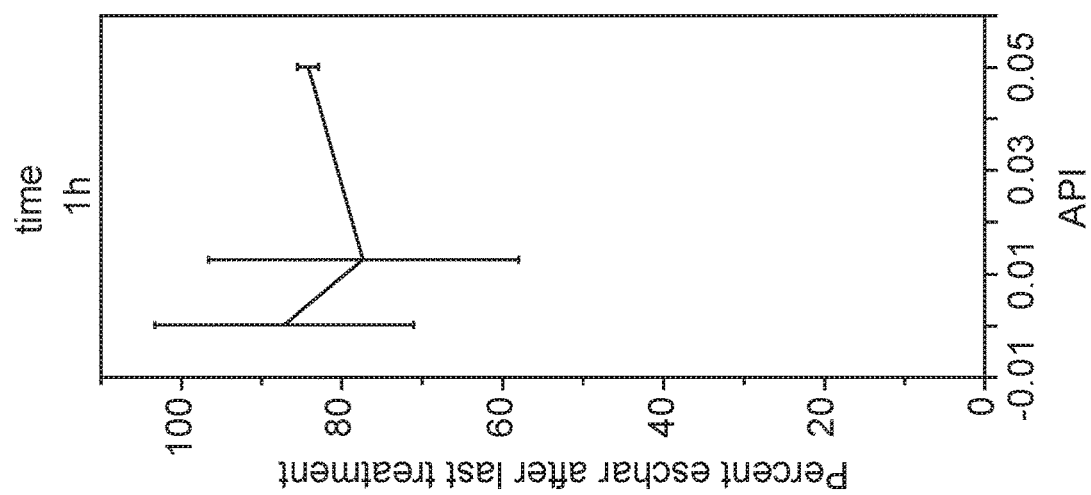

The percentage of eschar after the $10^{th}$ treatment was found to be significantly dependent on the amount of API in the gel formulation and the treatment duration. While in 1 hr treatments, there was no correlation between the amount of eschar at the $10^{th}$ treatment and the concentration of API (FIG. 2A), in the 4 hour treatments, the higher the concentration of API, the smaller the amount of eschar observed after the $10^{th}$ treatment (FIG. 2B). The 24 hour treatments showed that low concentrations of API in the gel formulation reduced the percent eschar in a concentration dependent manner; however, higher concentrations of API did not further decrease the percent of eschar (FIG. 2C).

Figure 3A:
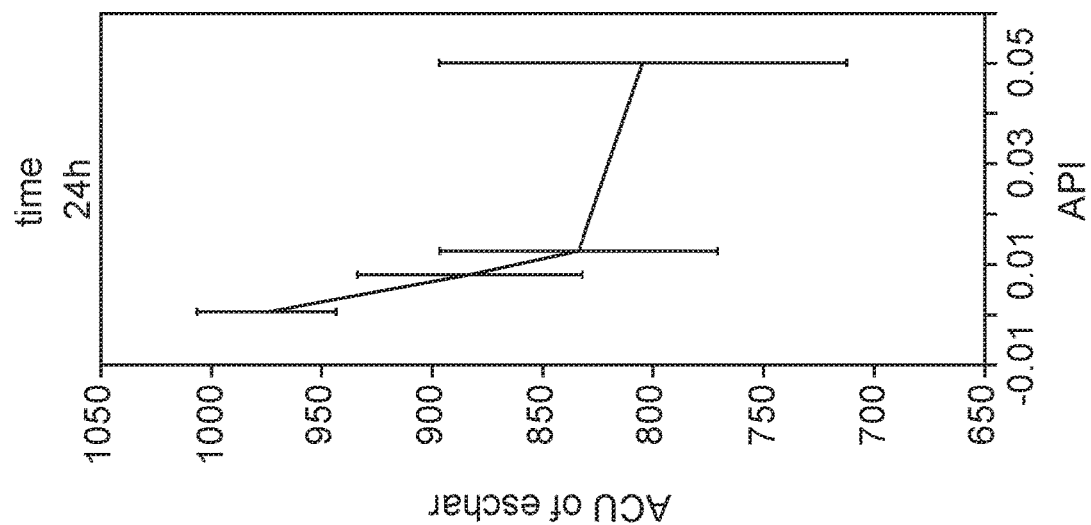
FIGS. 3A-C show the area under the curves (AUC) of eschar after the $10^{th}$ treatment with the EscharEx Gel as a function of the amount of API applied to the wound for 1 hour (FIG. 3A), 4 hours (FIG. 3B) and 24 hours (FIG. 3C).
Figure 3B:
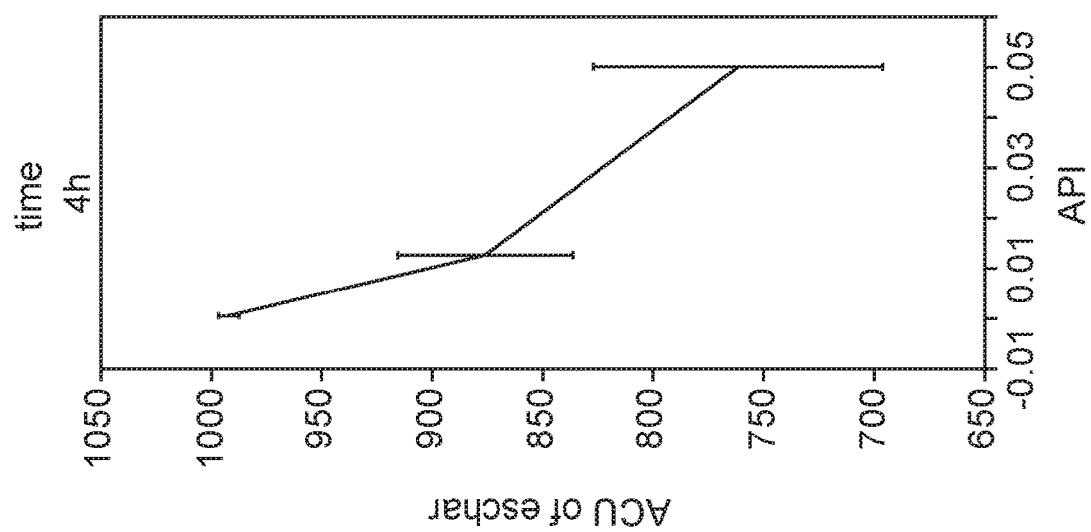
Figure 3C:
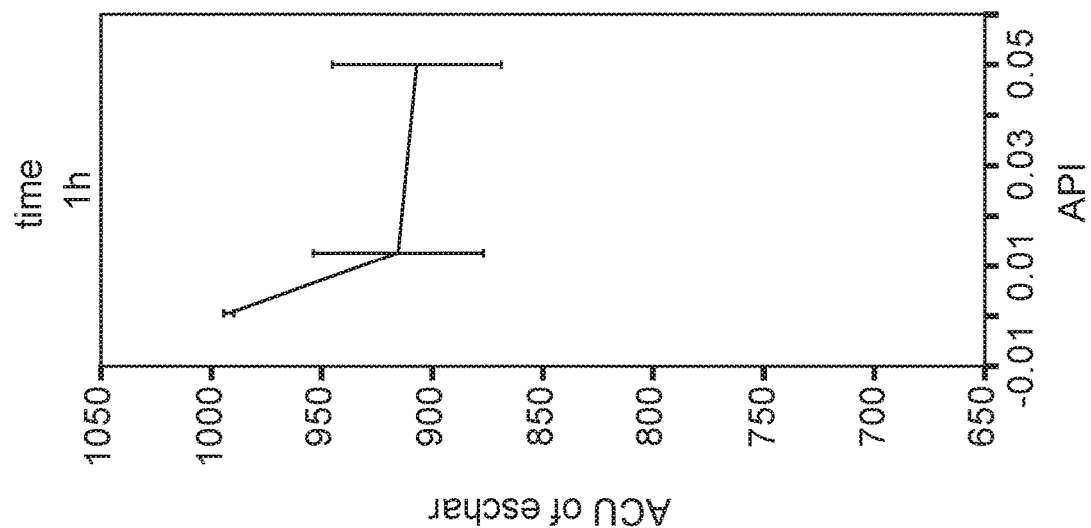

Debridement efficacy (AUC) was found to be significantly dependent on the API concentration and treatment duration. The 1 hour treatments were less effective than the 4 hour and the 24 hour treatments, at all the API concentrations measured (FIGS. 3A, 3B, and 3C, respectively). In the 4 hr treatments, the AUC correlated with the API concentrations (FIG. 3B), while in the 24 hour treatments, the AUC correlated only at the lower concentrations of API (FIG. 3C).

Figure 4B:
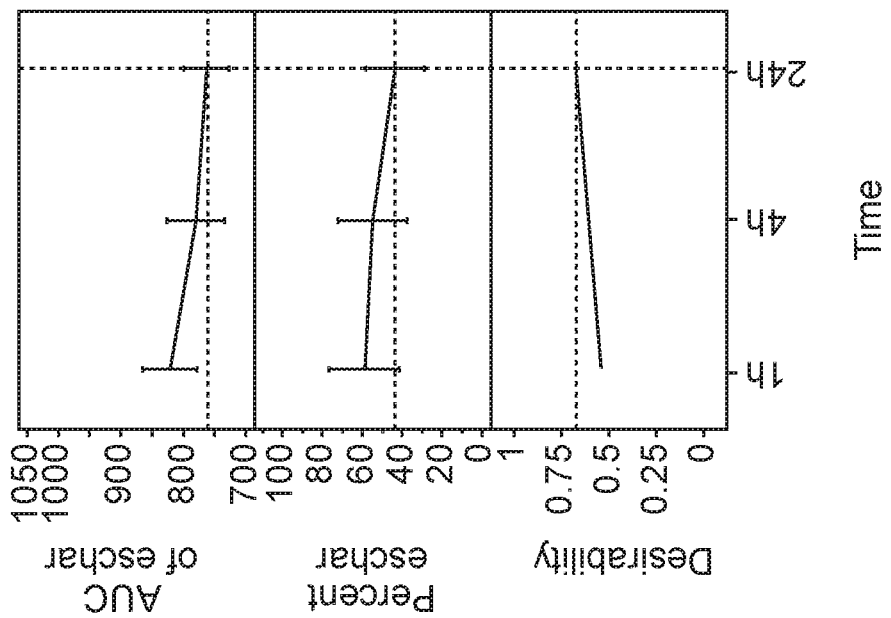
FIGS. 4A-B show a quadratic model of the area under the curve (AUC) of eschar (upper panels), percent of eschar after the $10^{th}$ treatment (middle panels) and the desirability function (optimization of lowest AUC and lowest eschar after the $10^{th}$ treatment; lower panels) as a function of the amount of API (FIG. 4A) and as a function of the treatment duration (FIG. 4B). Wide dash lines indicate confidence intervals (95%) of the model.
Figure 4A:
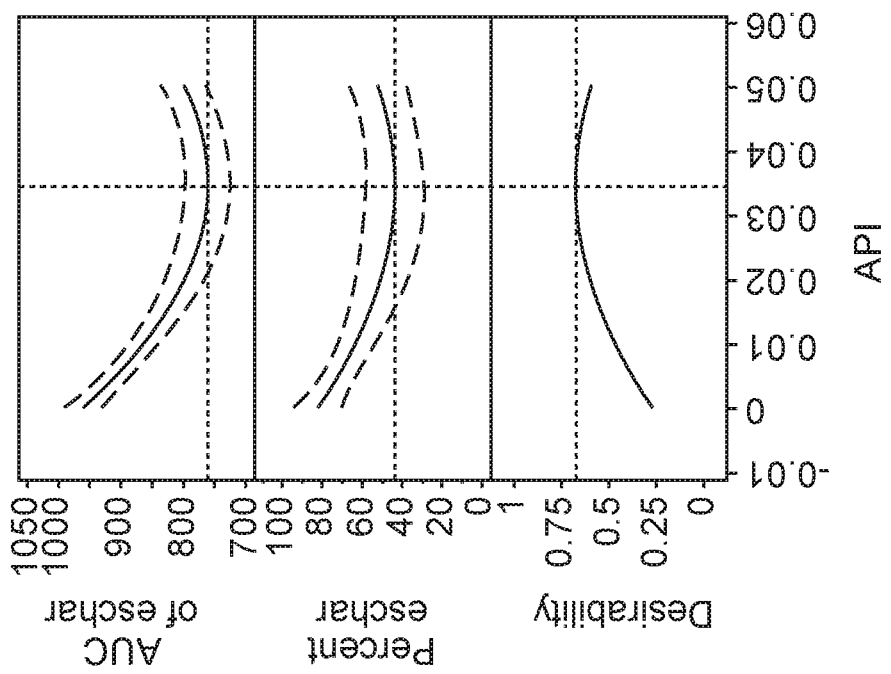

A fit to quadratic model (second order for API) for both the area under the curve of eschar (AUC; FIGS. 4A and 4B, upper panels) and the percent of eschar (FIGS. 4A and 4B, middle panels) after the $10^{th}$ treatment were found to be significant (p value 0.0154). According to this model, the maximal desirability function value (i.e., both the lowest percent of eschar and the lowest AUC after the last treatment) was reached in the 24 hour treatment at API concentration of ~3.5% (FIGS. 4A and 4B, lower panels).

The size of the wound barely changed during the treatment period and any change in size was very gradual. This applied to all treatment groups.

During the recovery period: both for the gel vehicle groups and EX01 groups, if the eschar remained after the $10^{th}$ treatment, it dried out and fell off the wound during the recovery period. Therefore, the percent eschar after the recovery period was 0 or close to 0 in all groups. There was no significant correlation between either the percent of eschar at the end of recovery period or the AUC during the recovery period and the API concentrations or treatment durations.

Once the eschar fell off, all wounds started to close. Therefore, no significant correlation was found between wound size out of the initial wound size and the API concentration or treatment duration. The same was true also for the AUC during the recovery period.

Conclusions

The results of this study indicated that eschar removal was significantly more efficient by the gel formulations containing API than by the gel vehicle at all the API concentrations and at all treatment durations. The optimum efficiency was found to be at about 3.5% w/w API in the 24 hour treatment, indicating that in 24 hour treatments higher API concentrations above 3.5% w/w of the total weight of the gel formulation did not lead to increased efficacy. The results of this study further indicated that in terms of efficacy and safety, longer treatment can be compensated by a lower concentration of the API.

Example 3

Efficacy and Safety of API in the Gel Formulation—Clinical Study

The aim of this study was to assess the efficacy and safety of the EscharEx Gel in preparing the wound's bed in subjects with hard to heal venous leg ulcers, diabetic lower extremity ulcers and traumatic/post-operative wounds.

A multicenter, randomized, vehicle-controlled, assessor blinded study was performed in subjects with hard to heal wounds to evaluate the efficacy and safety of the API in the gel formulation disclosed in Examples 1 and 2 herein above for preparing the wound's bed in patients with hard to heal venous leg ulcers, diabetic lower extremity ulcers and traumatic/post operative wounds.

The study included 73 subjects that were treated with EscharEx Gel or Gel Vehicle in up to 10 daily treatments, 4 hours±15 minutes application time each. This period was defined as the "Treatment period". Following each application, the wound was washed, photographed, and assessed clinically for wound size, removal of nonviable tissue and change in granulation tissue, wound status, and safety parameters. After each debridement treatment with the EscharEx Gel or Gel Vehicle the blinded assessor decided upon continuation of treatment, and wound was dressed with moist-to-moist saline gauze.

Following completion of the "Treatment period", subjects were treated according to standard procedures at their center and were evaluated (wound assessments) once a week until complete wound closure or for up to 12 weeks from last treatment application (total of up to 12 weekly follow-up visits).

For subjects who achieved wound closure, additional 3 monthly follow-up visits (3 visits in total) were conducted to assess wound closure recurrence. The overall duration of the study was up to 27 weeks.

Patients enrolled to this study were adult subjects with >50% necrotic/slough/fibrin nonviable tissue on a hard to heal wound (wound age 4 weeks or more) of the following etiologies: venous leg ulcers, diabetic lower extremity ulcers, and traumatic/post-operative wounds.

For the preparation of EscharEx Gel, two grams of EscharEx® sterile powder were mixed in 40 grams of sterile Gel vehicle as described herein abobe in Example 1 ≤15 min prior to use to obtain 5% EscharEx Gel. Following mixing of the powder with the Gel Vehicle, each gram of the prepared EscharEx Gel contained 0.05 g EscharEx powder. Per randomization allocation, 2 g powder mixed in 40 grams of Gel Vehicle (EscharEx Gel) or 40 g of Gel Vehicle only were applied to the wound surface per 200 $cm^2$ of wound surface.

Safety outcome was evaluated by determining severity and incidence of general and local adverse events, vital signs, pain assessment (using VAS), clinical signs of infection, safety laboratory parameters (blood chemistry, hematology, coagulation), physical examination, and blood loss.

For subjects receiving EscharEx Gel treatment, the following procedure was performed: Preventive analgesia using Lidocaine gel or a combination of Lidocaine 4%, Epinephrine 0.05%, Tetracaine 0.5% (LET gel) were applied on the skin edges and the wound itself for half an hour before EscharEx application. Skin surrounding the wound was protected by petrolatum ointment (on the wound edges). Sterile isotonic (0.9%) sodium chloride solution was sprinkled on the wound. The wound was kept moist during the application procedure. Following gel application, the wound was covered with an occlusive film dressing that adhered to the sterile adhesive barrier material applied. The EscharEx Gel filled the entire occlusive dressing, and special care was taken not to leave air in this occlusive dressing. The dressed wound was covered with a loose, fluffy bandage dressing that holds and stabilizes the occlusive dressing in place. The dressing remained in place for 4 hours and special care was given to protect and not disrupt the dressing. After 4 hours of treatment the occlusive dressing was removed using aseptic techniques. The adhesive barrier was removed using a sterile blunt-edged instrument (e.g. tongue depressor). The dissolved nonviable tissue was removed from the wound by wiping it away with dry gauze, tongue depressor etc. followed by wiping with wet gauze and then washing the wound with water.

Results

Incidence of Complete Debridement

As shown in Table 1, the incidence of complete debridement (≥90% non-viable tissue removal) at the end of the debridement period (up to 10 treatment days) was significantly higher in the EscharEx Gel group compared to the Gel Vehicle group, i.e., 55.1% vs. 29.2%, respectively, in the intent to treat (ITT) Population.

TABLE 1

Frequency of Complete Debridement by Treatment Group (ITT Population)

|  | Complete Debridement | | | | |
|---|---|---|---|---|---|
|  | Achieved | | Not Achieved | | |
|  | n | % | n | % | p value* |
| EscharEx (N = 49) | 27 | 55.1 | 22 | 44.9 | 0.047 |
| Gel Vehicle (N = 24) | 7 | 29.2 | 17 | 70.8 | |

*Two-sided Fisher exact test for comparison between groups

Analysis of the incidence of complete debridement according to wound etiology was also performed. As shown in Table 2, the difference between EscharEx Gel and Gel Vehicle groups was more pronounced in the 'diabetic lower extremity ulcer' etiology (50.0% vs. 14.3%, respectively) and in the 'venous leg ulcer' etiology (62.5% vs. 25.0%, respectively).

TABLE 2

Frequency of Complete Debridement by Etiology and Treatment Group (ITT Population)

|  |  | Complete Debridement | | | | |
|---|---|---|---|---|---|---|
|  |  | Achieved | | Not Achieved | | |
| Etiology |  | n | % | n | % | p value* |
| Diabetic Lower Extremity Ulcer | EscharEx (N = 16) | 8 | 50.0 | 8 | 50.0 | 0.176 |
|  | Gel Vehicle (N = 7) | 1 | 14.3 | 6 | 85.7 | |
| Venous Leg Ulcer | EscharEx (N = 16) | 10 | 62.5 | 6 | 37.5 | 0.193 |
|  | Gel Vehicle (N = 8) | 2 | 25.0 | 6 | 75.0 | |
| Traumatic/Post Surgery Wounds | EscharEx (N = 17) | 9 | 52.9 | 8 | 47.1 | 1.000 |
|  | Gel Vehicle (N = 9) | 4 | 44.4 | 5 | 55.6 | |

*2-sided Fisher exact test for comparison between groups

Analysis of the frequency of complete debridement in the combined patient populations of 'diabetic lower extremity ulcer' and 'venous leg ulcer' (excluding patients with 'traumatic/post-surgery wounds') resulted in a more significant effect of the EscharEx Gel compared to the Gel Vehicle (frequency of complete debridement 56.3% vs. 20.0%, respectively, p=0.028; Table 3).

TABLE 3

Frequency of Complete Debridement in combined patient population of Diabetic Lower Extremity Ulcer and Venous Leg Ulcer, by Treatment Group (ITT Population)

|  | Complete Debridement | | | | |
|---|---|---|---|---|---|
|  | Achieved | | Not Achieved | | |
|  | n | % | n | % | p value* |
| EscharEx (N = 32) | 18 | 56.3 | 14 | 43.8 | 0.028 |
| Gel Vehicle (N = 15) | 3 | 20.0 | 12 | 80.0 | |

*2-sided Fisher exact test for comparison between groups

Time to Complete Debridement

Figure 5:
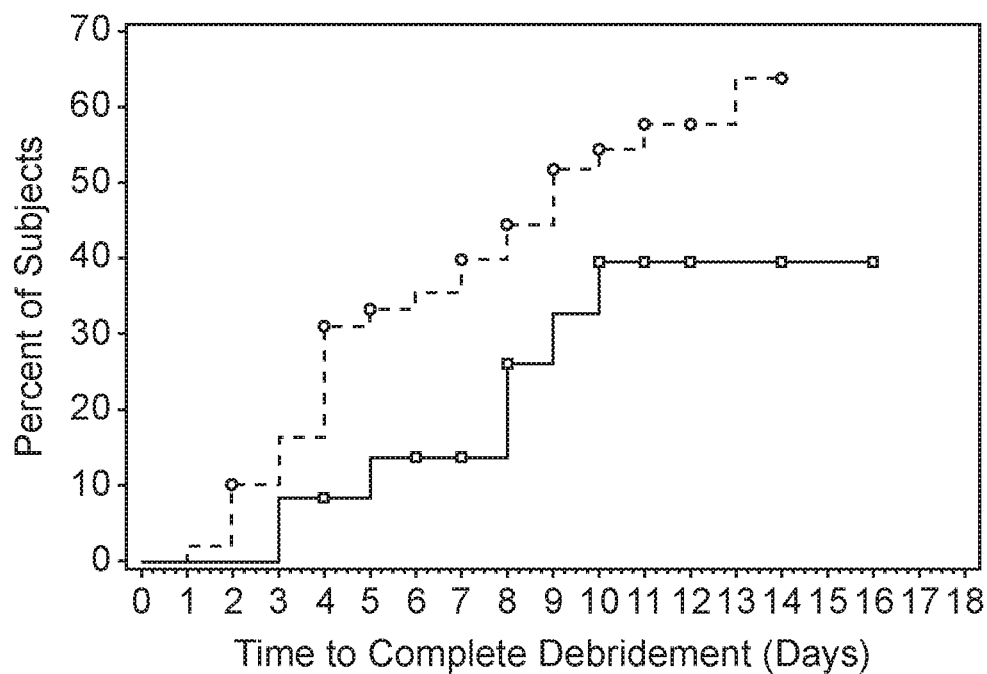
FIG. 5 shows time to complete debridement by treatment group in Intention-to-Treat (ITT) Population.

Mean time to complete debridement in ITT population within 10 treatment days was shorter in the EscharEx Gel group (mean 7.6 days) compared to the Gel Vehicle group (mean 8.4 days). FIG. 5 shows Kaplan-Meier plot of time to complete debridement by treatment group. Percent of patients who achieved complete debridement at each time point was higher in the EscharEx Gel group compared to the Gel Vehicle group (Log Rank test p=0.075).

Figure 6:
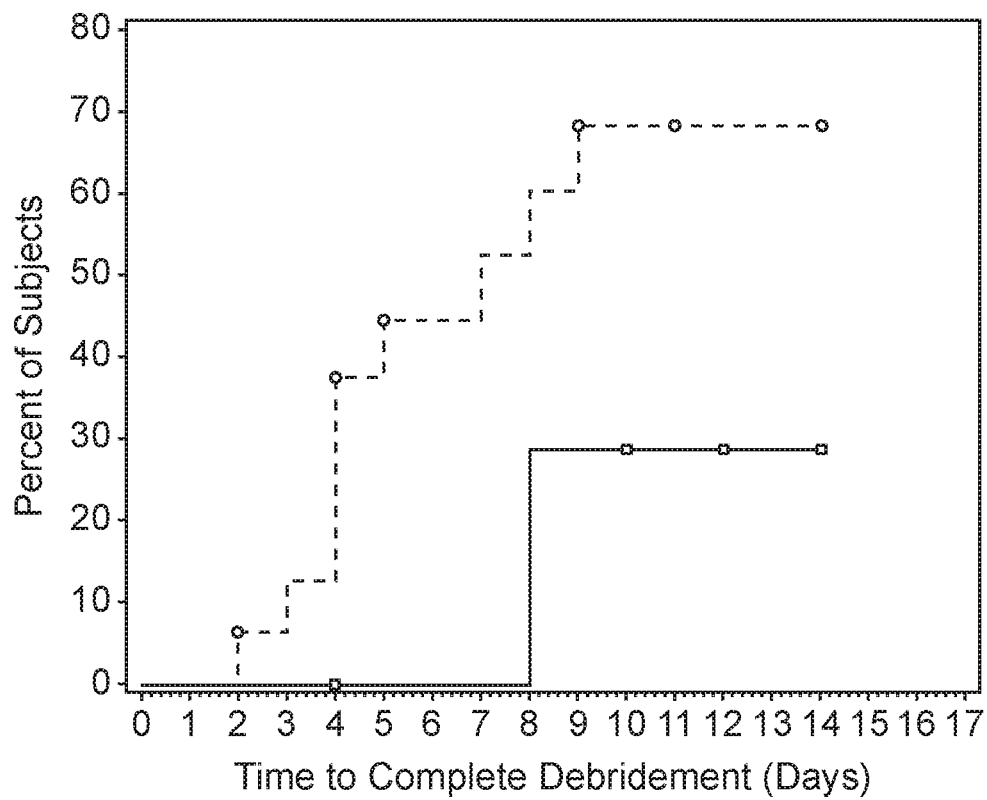
FIG. 6 shows time to complete debridement by treatment group in subjects suffering from venous leg ulcers in the ITT population.
Figure 7:
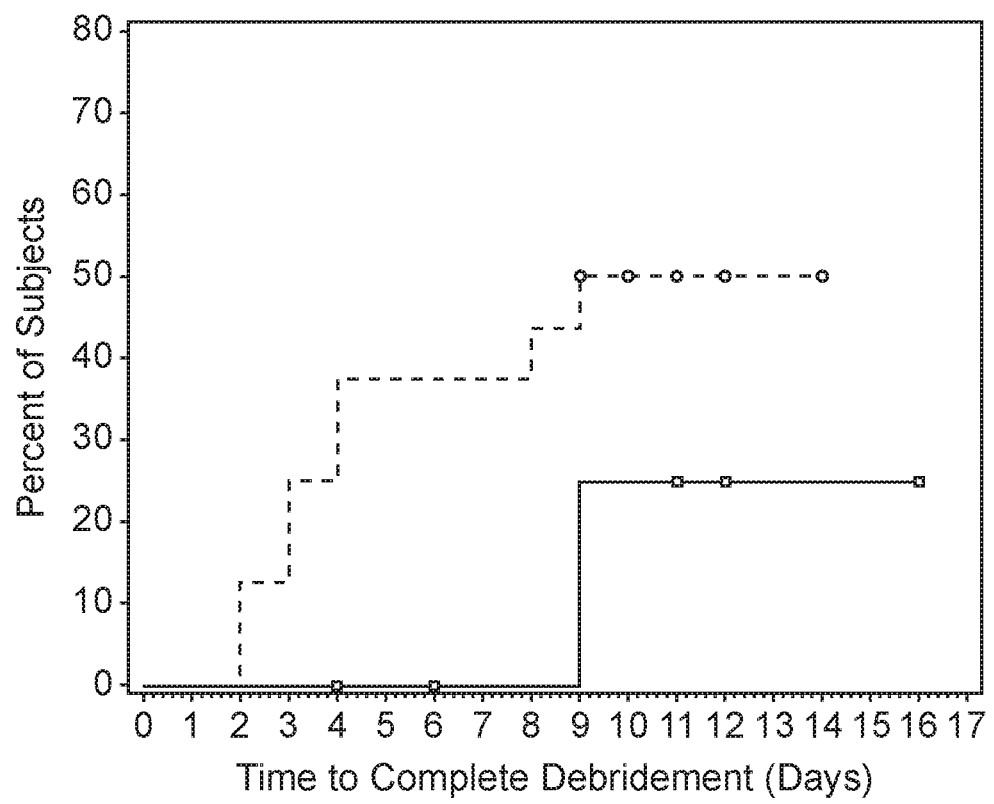
FIG. 7 shows time to complete debridement by treatment group in subjects suffering from diabetic lower extremity ulcers in the ITT population.

Subgroup analysis by etiology indicated that the mean time-to complete debridement was shorter in the EscharEx Gel group compared to the Gel Vehicle group in patients with 'venous leg ulcer' (mean 6.7 vs. 10.5 days, respectively) and 'diabetic lower extremity ulcer' (mean 7.9 vs. 8.9 days, respectively). Kaplan-Meier plots of time-to complete debridement are presented in FIG. 6 for 'venous leg ulcer' and in FIG. 7 for 'diabetic lower extremity ulcer'. Analysis of the combined two populations: 'diabetic lower extremity ulcer' and 'venous leg ulcer', resulted in a significant shorter time to complete debridement in the EscharEx Gel group (mean 7.3 days) compared to the Gel Vehicle group (mean 9.7 days).

Number of Applications to Complete Debridement

Table 4 shows percent of subjects with complete debridement by visit in the ITT population.

TABLE 4

Percent of Subjects with Complete Debridement by Visit

|  | EscharEx (N = 49) | | | Gel Vehicle (N = 24) | | |
|---|---|---|---|---|---|---|
| Visit | n | % | Cumulative Percent | n | % | Cumulative Percent |
| 1 | 1 | 2.0% | 2.0% | 0 | 0.0% | 0.0% |
| 2 | 4 | 8.2% | 10.2% | 0 | 0.0% | 0.0% |
| 3 | 3 | 6.1% | 16.3% | 2 | 8.3% | 8.3% |
| 4 | 8 | 16.3% | 32.7% | 0 | 0.0% | 8.3% |
| 5 | 2 | 4.1% | 36.7% | 1 | 4.2% | 12.5% |
| 6 | 3 | 6.1% | 42.9% | 3 | 12.5% | 25.0% |
| 7 | 4 | 8.2% | 51.0% | 1 | 4.2% | 29.2% |
| 8 | 1 | 2.0% | 53.1% | 0 | 0.0% | 29.2% |
| 9 | 1 | 2.0% | 55.1% | 0 | 0.0% | 29.2% |
| 10 | 0 | 0.0% | 55.1% | 0 | 0.0% | 29.2% |
| Not achieved * | 22 | 44.9% | 100.0% | 17 | 70.8% | 100.0% |
| All | 49 | 100.0% | 100.0% | 24 | 100.0% | 100.0% |

As shown in Table 4, total of 32.7% of subjects in the EscharEx Gel group achieved complete debridement within 4 treatment days compared to 8.3% in the Gel Vehicle group. More than half (51.0%) achieved complete debridement within 7 treatment days in the EscharEx Gel group compared to less than third of subjects (29.2%) in the Gel Vehicle group. In 25 of 27 patients (93%) who achieved complete debridement in the EscharEx Gel group complete debridement was achieved within 7 applications.

Subgroup analysis of percent of subjects with complete debridement by etiology in the ITT population indicated that half of subjects with 'diabetic lower extremity ulcer' and 'venous leg ulcer' achieved complete debridement within 7 and 5 days in the EscharEx Gel group, respectively; in the Gel Vehicle group, only 14.3% and 25.0% achieved complete debridement after 7 treatment days, respectively. In subjects with 'traumatic post-operative wounds' 52.9% achieved complete debridement only after 9 treatment days with the EscharEx Gel compared to 44.4% in the Gel Vehicle group.

Area of Non-Viable Tissue

Mean area of non-viable tissue prior to the 'Treatment period' was 25.3 cm$^2$ in the EscharEx Gel group and 22.7 cm$^2$ in the Gel Vehicle group. Percent reduction in non-viable tissue was greater in the EscharEx Gel group compared to the Gel Vehicle group at all study visits in the ITT population. At the end of the treatment period, mean relative reduction in area of non-viable tissue was 67.4% in the EscharEx Gel group vs. 46.0% in the Gel Vehicle group.

Analysis of mean area of non-viable tissue by etiology indicated that in all etiologies, there was greater reduction in mean area of non-viable tissue in the EscharEx Gel group compared to the Gel Vehicle group at all time points.

Safety

The majority of patients in this study experienced mild and moderate AEs accounted for 85.0% (130/153) of the reported AEs. Forty-four serious adverse events (SAEs) were reported; the proportion of patients reporting SAEs was similar across both groups, 39% (19/49) in the EscharEx Gel group vs. 33% (8/24) in Gel Vehicle group. Most patients who reported AEs (93.5%) experienced unrelated AEs (87.6%); remotely related AEs accounted for less than 5% of the AEs (7/153) and possibly related, probably related and related AEs accounted for less than 10% of the AEs. There were no AEs leading to premature discontinuation from the treatment.

The most common local AEs which were reported for ≥5% of patients in either study group, were under SOC 'injury, poisoning and procedural complications' (wound complication and wound dehiscence) and 'infection and infestations' (cellulitis and wound infection). In the overall study population, general AEs were reported for ≥5% of subjects in either study group in SOC 'general disorders and administration site conditions' (pyrexia), 'blood and lymphatic system disorders' (anaemia), 'gastrointestinal disorders' (constipation and nausea), 'skin and subcutaneous tissue disorders' (pruritus) and 'metabolism and nutrition disorders' (hypokalemia).

Evaluation of laboratory parameters (blood chemistry, hematology and coagulation factors), vital signs (blood pressure, pulse rate and temperature), physical examination and concomitant medication use did not reveal any apparent difference between the EscharEx Gel group and the Gel Vehicle group. There were no consistent or cumulative changes. Most laboratory abnormalities were present prior to the study.

Pain scores were nearly identical between study treatment groups across treatment visits, with minimal changes pre- and post-application. There was minimal evidence of severe infection (evaluated via clinical signs for cellulitis/osteomyelitis) during the treatment period.

Thus, EscharEx Gel therapy was well-tolerated and was not associated with notable pathological changes in the body system evaluated or with consistent changes in laboratory parameters, vital signs, pain assessment and concomitant medication use.

Conclusions

The study confirms that 5% EscharEx Gel is an efficacious enzymatic removal agent in the treatment of hard to heal wounds. It offers clinical benefit of effective and rapid nonsurgical debridement treatment for chronic wounds, particularly for diabetic lower extremity ulcers and venous leg ulcers.

Example 4

Efficacy and Safety of API in the Gel Formulation—Clinical Study

A multicenter, prospective, randomized, controlled, assessor blinded study is performed in subjects with hard to heal wounds to evaluate the efficacy and safety of the API in the gel formulation disclosed in Examples 1 and 2 herein above for preparing the wound's bed in patients with hard to heal ulcers.

The study includes 32 subjects (with 2 etiologies only; venous leg ulcers and diabetic lower extremity ulcers) that are treated by EscharEx Gel or Gel vehicle. Overall, 20 patients are treated in 24±2 hours application time (first cohort) and 12 subjects in 48±2 hours application time (second cohort) in up to 8 applications. Following completion of the "Treatment period", patients are treated according to standard procedures and evaluated (wound assessments) once a week until complete wound closure for up to 12 weeks from last application (up to 12 visits). Wound closure, if occurs, is confirmed 2 weeks after the last weekly visit. The overall duration of this study is up to 19 weeks The study population includes adults with >50% necrotic/slough/fibrin nonviable tissue on a hard to heal wound of the following etiologies:
1. Venous leg ulcers
2. Diabetic lower extremity ulcers Following each application of the EacharEx Gel or Gel vehicle, the wound is washed, photographed and assessed for wound size, removal of nonviable tissue and change in granulation tissue (by digital planimetry software), wound status, and safety parameters. Subsequent to each debridement treatment the wound is dressed with moist-to-moist saline gauze.

Two grams of Debrase® sterile powder are mixed in 40 grams of sterile gel vehicle (ratio of 1:20) ≤15 min prior to use to obtain EscharEx Gel.

Following mixing of the powder with the gel vehicle, each gram of the prepared EscharEx Gel contains 0.05 g EscharEx® powder.

Per allocation, 2 gr powder mixed in 40 grams of the gel vehicle (EscharEx Gel) or 40 g of the gel vehicle only, as per the randomization arm, are applied to the wound surface per 200 cm$^2$ of wound surface, for 24±1 hours and 48±2 hours (2 treatment arms) on each application, and up to 10 applications or until complete debridement achieved, whichever occurs first.

The Inclusion Criteria are as follows:
1. Patients, men or women, between 18 and 90 years of age;
2. Patient with venous leg ulcer or diabetic (lower extremity) ulcer or traumatic/post operative wound (determined by medical history and physical examination);

3. Wound is not healing for at least 4 weeks;
4. The necrotic/slough/fibrin non-viable tissue area is at least 50% of wound area (assessed by clinical evaluation);
5. Wound surface area (length×width) is in the range of 5-200 cm$^2$;

The primary endpoint is the incidence of complete debridement (non-viable tissue removal) at the end of the debridement period (up to 10 treatments).

The secondary endpoints include:
1. Time to achieve complete debridement (up to 10 treatments) (survival analysis);
2. Number of applications to achieve complete debridement;
3. Time to achieve >75% debridement (up to 10 treatments);
4. Incidence of >75% debridement (up to 10 treatments);
5. Assessment of changes in wound debridement status during treatment period: percentage reduction in non viable tissue (daily, during 10 treatments);
6. Time to achieve wound bed prepared for healing and closure: bed that can be successfully auto grafted;
7. Time to achieve complete granulation and time to achieve >75% granulation (up to 12 weeks);
8. Incidence of complete granulation and incidence of >75% granulation (on week 12);
9. Percent of change in granulation tissue over time (weekly, during baseline-12 weeks);
10. Incidence of complete wound closure (up to 12 weeks);
11. Time to complete wound closure (up to 12 weeks);
12. Wound area reduction: percentage reduction in wound size over time (weekly, from baseline up to 12 weeks);
13. Changes in the condition of the wound (wound healing status) as assessed by The Leg Ulcer Measurement Tool (LUMT) (end of debridement and end of wound closure follow-up);
14. Change in Quality of Life as assessed by the SF-36 (end of wound closure follow-up and 3 months post wound closure follow-up period);
15. Recurrence rate of wounds (3 months after wound closure);
16. Time to recurrence of wounds (during 3 months after closure).

Safety outcome measures are evaluated. Such measures include: severity and incidence of systemic and local adverse events, vital signs, pain assessment (using VAS), evidence of infection, clinical laboratory parameters (blood chemistry, hematology, coagulation), physical examination, and blood loss.

It will be appreciated by persons skilled in the art that the present invention is not limited by what has been particularly shown and described herein above. Rather the scope of the invention is defined by the claims that follow.

What is claimed is:

1. A method for debridement of a chronic or hard to heal wound comprising a step of applying to a site of the chronic or hard to heal wound in a subject in need of such treatment a therapeutically effective amount of a debriding composition comprising:
   (a) a proteolytic enzyme mixture obtained from bromelain comprising stem bromelain (EC 3.4.22.32), ananain (EC 3.4.22.31), a cysteine protease precursor, and jacalin-type lectin, the proteolytic enzyme mixture being in a dry or lyophilized form;
   (b) a pH adjusting agent; and
   (c) a carrier comprising:
      (i) a carbomer present in an amount of about 0.9% (w/w) of the total weight of the carrier;
      (ii) a polar co-solvent which is glycerol present in an amount of about 10% (w/w) of the total weight of the carrier; and
      (iii) water,
   wherein the proteolytic enzyme mixture (a) is admixed with the pH adjusting agent (b) and the carrier (c) to form the debriding composition in the form of a gel that has a viscosity in the range of about 15,000 centipoise (cP) to about 25,000 cP and a pH ranging from about 6.0 to about 8.0,
   wherein said proteolytic enzyme mixture is present in the debriding composition in an amount ranging from about 1% (w/w) to about 5% (w/w) of the total weight of the carrier,
   wherein the step of applying said debriding composition is performed in a regimen of two applications to up to ten applications, and
   wherein the debriding composition is maintained in contact with the wound site for at least about 4 hours to about 72 hours per application.

2. The method according to claim 1, wherein the pH adjusting agent is selected from the group consisting of sodium phosphate, sodium carbonate, and potassium carbonate.

3. The method according to claim 2, wherein the sodium phosphate is anhydrous di-sodium hydrogen phosphate.

4. The method according to claim 1, wherein the chronic or hard to heal wound is selected from the group consisting of a diabetic ulcer, a venous stasis ulcer, an arterial insufficiency ulcer, a pressure ulcer, a post-operative wound, and a post-trauma wound.

5. The method according to claim 1, wherein the debriding composition is maintained in contact with the wound site for about 24 hours per application.

6. The method according to claim 1, wherein the debriding composition is maintained in contact with the wound site for about 48 hours per application.

7. The method according to claim 1, wherein applying the debriding composition is performed three times a week for at least one week, and wherein the debriding composition is maintained in contact with the wound site for a duration selected from the group consisting of 48 hours per application and 72 hours per application.

8. The method according to claim 1, wherein the debriding composition is maintained in contact with the wound site for about 72 hours per application.

9. The method according to claim 1, wherein the number of applications and time of contact of the debriding composition with the wound site are conducted to achieve complete wound debridement and/or wound closure.

10. A method for debridement of a chronic or hard to heal wound comprising a step of applying to a site of the chronic or hard to heal wound in a subject in need of such treatment a therapeutically effective amount of a debriding composition comprising:
    (a) a proteolytic enzyme mixture obtained from bromelain comprising stem bromelain (EC 3.4.22.32), ananain (EC 3.4.22.31), a cysteine protease precursor, and jacalin-type lectin, the proteolytic enzyme mixture being in a dry or lyophilized form;
    (b) a carrier comprising:
       (i) a carbomer present in an amount of about 0.9% (w/w) of the total weight of the carrier;

(ii) a polar co-solvent which is glycerol present in an amount of about 10% (w/w) of the total weight of the carrier; and (iii) a pH adjusting agent which is anhydrous di-sodium hydrogen phosphate present in an amount of about 0.25% (w/w) of the total weight of the carrier; and (iv) water, wherein the proteolytic enzyme mixture (a) is admixed with the carrier (b) to form the debriding composition in the form of a gel that has a viscosity ranging from about 15,000 cP to about 25,000 cP and a pH ranging from about 6.0 to about 7.0, wherein said proteolytic enzyme mixture is present in an amount ranging from about 1% (w/w) to about 5% (w/w) of the total weight of the carrier, wherein the step of applying said debriding composition is performed in a regimen of two applications to up to ten applications, and wherein the debriding composition is maintained in contact with the wound site for at least about 4 hours to about 72 hours per application.

11. The method according to claim 10, wherein the chronic or hard to heal wound is selected from the group consisting of a diabetic ulcer, a venous stasis ulcer, an arterial insufficiency ulcer, a pressure ulcer, a post-operative wound, and a post-trauma wound.

12. The method according to claim 10, wherein the debriding composition is maintained in contact with the wound site for about 24 hours per application.

13. The method according to claim 10, wherein the debriding composition is maintained in contact with the wound site for about 48 hours per application.

14. The method according to claim 10, wherein the debriding composition is maintained in contact with the wound site for about 72 hours per application.

15. The method according to claim 10, wherein the number of applications and time of contact of the debriding composition with the wound site are conducted to achieve complete wound debridement and/or wound closure.

16. A method for complete debridement and/or wound closure of a chronic or hard to heal wound comprising a step of applying to a site of the chronic or hard to heal wound in a subject in need of such treatment a therapeutically effective amount of a debriding composition comprising:

(a) a proteolytic enzyme mixture obtained from bromelain comprising stem bromelain (EC 3.4.22.32), ananain (EC 3.4.22.31), a cysteine protease precursor, and jacalin-type lectin, the proteolytic enzyme mixture being in a dry or lyophilized form;

(b) a pH adjusting agent; and (c) a carrier comprising:

(i) a carbomer present in an amount of about 0.9% (w/w) of the total weight of the carrier;

(ii) a polar co-solvent which is glycerol present in an amount of about 10% (w/w) of the total weight of the carrier; and (iii) water, wherein the proteolytic enzyme mixture (a) is admixed with the pH adjusting agent (b) and the carrier (c) to form the debriding composition in the form of a gel that has a viscosity in the range of about 15,000 centipoise (cP) to about 25,000 cP and a pH ranging from about 6.0 to about 8.0, wherein said proteolytic enzyme mixture is present in the debriding composition in an amount ranging from about 1% (w/w) to about 5% (w/w) of the total weight of the carrier, wherein the step of applying said debriding composition is performed in a regimen of two applications to up to ten applications, with the debriding composition maintained in contact with the wound site for at least about 4 hours to about 72 hours per application with the number of applications and time of contact of the debriding composition with the wound site conducted to achieve complete wound debridement and/or wound closure.

* * * * *